(12) United States Patent
Bardakjian et al.

(10) Patent No.: US 9,314,623 B2
(45) Date of Patent: Apr. 19, 2016

(54) SYSTEM AND METHOD FOR COGNITIVE RHYTHM GENERATION

(75) Inventors: Berj L. Bardakjian, Toronto (CA); Osbert C. Zalay, Toronto (CA)

(73) Assignee: Neurochip Corporation of C/O ZBX Corporation, Toronto, Ontario (CA)

( * ) Notice: Subject to any disclaimer, the term of this patent is extended or adjusted under 35 U.S.C. 154(b) by 928 days.

(21) Appl. No.: 12/707,601

(22) Filed: Feb. 17, 2010

(65) Prior Publication Data

US 2010/0292752 A1 Nov. 18, 2010

Related U.S. Application Data

(60) Provisional application No. 61/153,187, filed on Feb. 17, 2009, provisional application No. 61/166,912, filed on Apr. 6, 2009.

(51) Int. Cl.
*A61N 1/36* (2006.01)
*A61B 5/04* (2006.01)

(52) U.S. Cl.
CPC ........ *A61N 1/36025* (2013.01); *A61N 1/36064* (2013.01); *A61B 5/04012* (2013.01); *A61N 1/36082* (2013.01)

(58) Field of Classification Search
CPC ........... A61N 1/36025; A61N 1/36082; A61N 1/36404; A61N 1/3606; A61N 1/36; A61B 5/04012; A61B 5/0476; A61B 5/4094
USPC .............................. 607/2, 45; 600/9, 544, 545
See application file for complete search history.

(56) References Cited

U.S. PATENT DOCUMENTS

| 5,101,828 | A | | 4/1992 | Welkowitz et al. | |
|---|---|---|---|---|---|
| 5,402,797 | A | * | 4/1995 | Akiyama et al. | ............... 600/545 |
| 5,857,978 | A | * | 1/1999 | Hively et al. | .................. 600/544 |
| 2005/0124848 | A1 | * | 6/2005 | Holzner | ............................ 600/9 |

OTHER PUBLICATIONS

Vasilis Marmarelis, "Signal Transformation and Coding in Neural Systems," IEEE Transactions on Biomedical Engineering, vol. 36, No. 1, Jan. 1989, pp. 15-24.
Osbert Zalay et al., "Mapped Clock Oscillators as Ring Devices and Their Application to Neuronal Electrical Rhythms," IEEE Transactions on Neural Systems and Rehabilitation Engineering, vol. 16, No. 3, Jun. 2008, pp. 233-244.
International Search Report and Written Opinion dated Jun. 16, 2010.
English Translation of Office Action for corresponding Chinese Application No. 201080008195.4 dated Apr. 1, 2013.

* cited by examiner

*Primary Examiner* — Christopher D Koharski
*Assistant Examiner* — Pamela M Bays
(74) *Attorney, Agent, or Firm* — Harness, Dickey & Pierce

(57) ABSTRACT

A method of modeling time-dependent electrical activity of a biological system, the method comprises transforming an input through at least one dynamic mode to yield at least one modal output; processing the at least one modal output to yield at least one amplitude variable and at least one phase variable; and mapping the at least one amplitude variable and the at least one phase variable to an observable output.

20 Claims, 24 Drawing Sheets

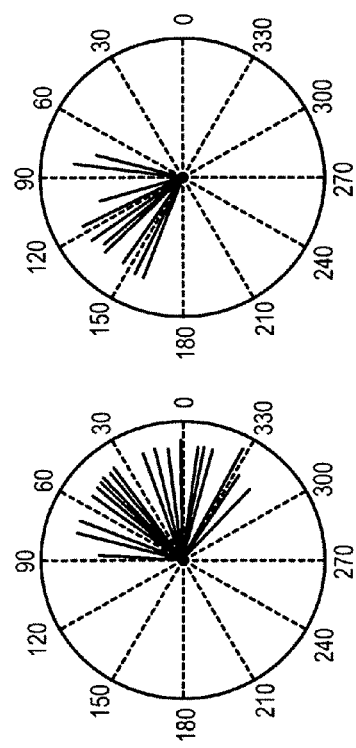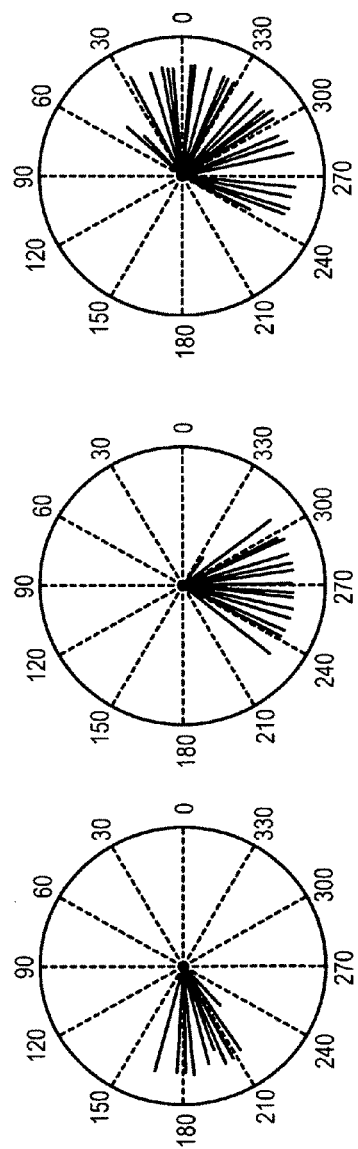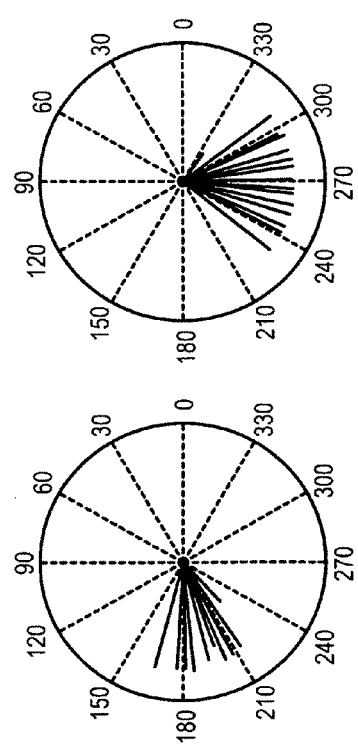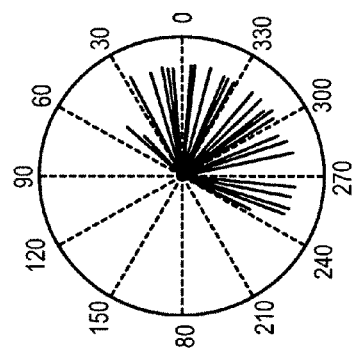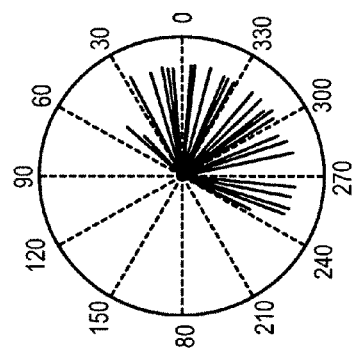
FIG. 4D
FIG. 4E
FIG. 4F
FIG. 4G
FIG. 4H

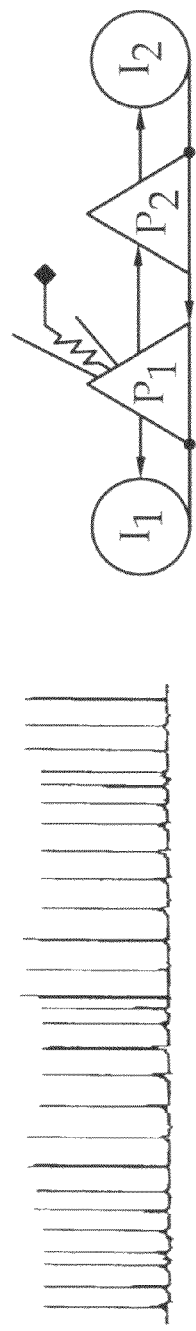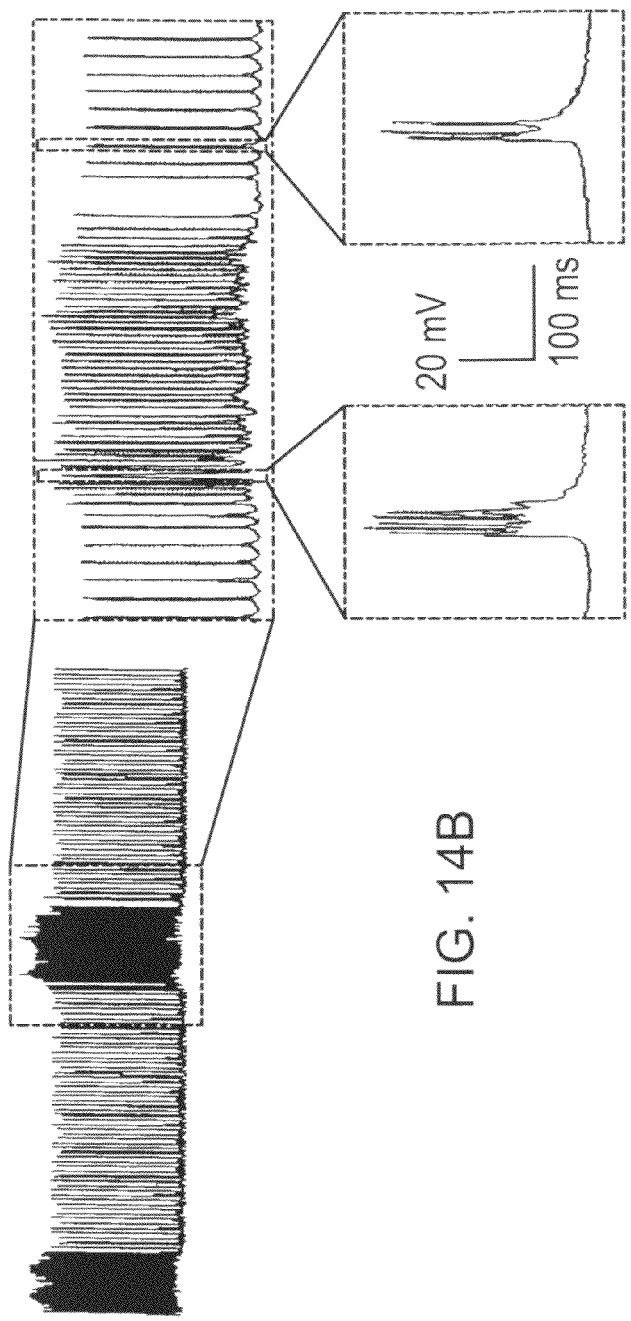
FIG. 14A
FIG. 14B

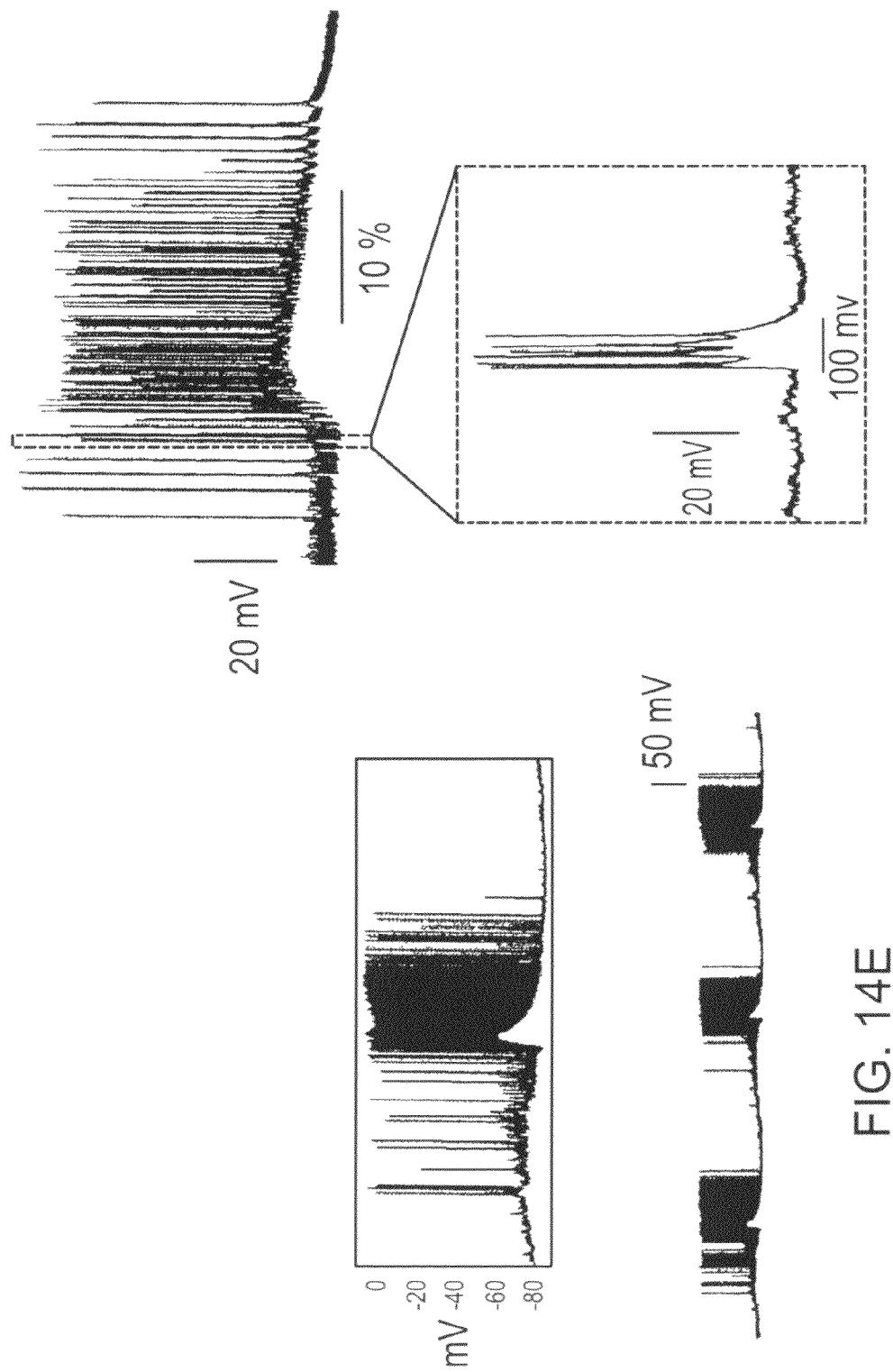

SYSTEM AND METHOD FOR COGNITIVE RHYTHM GENERATION

CROSS-REFERENCE TO RELATED APPLICATIONS

This application claims the benefit of U.S. Provisional Application No. 61/153,187 filed on Feb. 17, 2009 entitled "System and Method for Cognitive Rhythm Generation" and U.S. Provisional Application No. 61/166,912 filed on Apr. 6, 2009 entitled "System and Method for Cognitive Rhythm Generation", the contents of which are incorporated herein by reference in their entirety.

FIELD OF THE INVENTION

The present invention relates generally to neural coding and in particular to a method of modeling time-dependent electrical activity of a biological system, to a cognitive rhythm generator, and to a method of controlling or treating a seizure-like event.

BACKGROUND OF THE INVENTION

Neural coding refers to how sensory and other information is represented in the brain by neurons. Neurons have been observed to coordinate their firing activity in accordance with the phase of a secondary process, including neuronal field oscillations, external sensory stimuli, and body orientation and/or displacement. This specific form of neural coding is referred to as "phase coding".

Phase coding appears to be a universal coding trait, manifesting across different organisms and processes. For example, cells in the rodent thalamus and postsubiculum are sensitive to head direction and the activity of different neurons maps to different phases of rotation over the entire 360 degree range. Similarly, cells in the posterior parietal cortex of the macaque monkey respond to vestibular stimuli, coding for a mixture of angular position, velocity, and acceleration. In the blowfly, optic lobe neurons display sensitivity to the motion of visual stimuli and the preferred direction changes with the location of the stimulus over the blowfly's visual field. In the rat hippocampus, gamma-frequency activity from different interneuronal groups was shown to be preferential to different phases of the population theta oscillation, with axo-axonic cells discharging just after the peak crest, oriens-lacunosum-moleculare cells activating on the trough, and parvalbumin-expressing basket cells firing on the descending edge of the theta wave.

The nature of phase coding is dynamic, as phase relationships may change over time. One example is the phenomenon of phase precession, which is a phenomenon of cell firing relative to a "place field". Place fields are receptive fields corresponding to specific locations in an animal's environment. In the hippocampus, neurons are organized according to place fields. Phase precession is described as a shift in the timing of neuronal firing relative to the local theta rhythm, such that the firing occurs at earlier phases of the theta cycle as an animal passes through a cell's place field. Place field ensembles undergo phase precession and are understood to constitute a cognitive map for navigation. Many studies have implicated the importance of phase precession with regard to the formation and recall of cognitive maps.

Phase selectivity and phase precession are related, sharing a common framework that underpins neural phase coding in general. This framework is the product of both cellular and network mechanisms, such as small molecule signaling, synaptic transmission, electric field coupling, and gap junction coupling. From a systems perspective, however, it is not necessary to characterize these mechanisms explicitly. Their transformative effects may be represented by functional blocks, allowing for a high-level description of neural coding without having to consider microscopic properties or connectivity. Conventional measurement of nonlinear system-level properties and therefore neural coding attributes is achieved by identification of Wiener or Volterra kernel models to map the input-output dynamics of the system. Kernel models of neuronal pathways have yielded insight into how motor and sensory pathways code limb movement, direction, auditory and visual information. Input-output relationships in thalamocortical and hippocampal circuits have also been mapped using similar models.

However, the brain is both a complex signal processor and a generator of rhythmic signals internal to the system. As such, the brain cannot be adequately described using a purely generative model (such as a coupled oscillator model without inputs) or a pure input-output map (such as a Volterra kernel model). Despite the success of kernel models, they cannot account for all forms of neural activity. For example, kernel models cannot account for spontaneous activity lacking an extrinsic trigger, and activity possessing indefinite memory, such as intrinsic oscillations. Rhythms in the brain carry information and their role in neural coding and communication cannot be ignored. Certain neural coding phenomena, such as phase precession, rely strictly on the presence of population oscillations. For example, gamma activity (30-80 Hz) phase-coordinated with the theta rhythm (3-10 Hz) occurs during spatial navigation and is implicated in the formation of hippocampal place fields. Super-gamma ripples (100-300 Hz) superimposed on sharp waves arise during slow-wave sleep (<1 Hz) and are purported to be involved in consolidation of memories in the cortex. The rhythmicity of cortical and hippocampal circuits is attributable to interactions amongst coupled network oscillators consisting of independently rhythmic neuronal subpopulations.

The traditional approach to neural modeling is anchored at the cellular realm, with a single neuron serving as the fundamental network unit. Cellular-level models are robust when the specific properties and connectivity of individual neurons within the network can be established beforehand by measurement or deduction. Examples of such models include classical conductance-based models (Hodgkin and Huxley, A quantitative description of membrane current and its application to conduction and excitation in nerve, J Physiol, 117:500-44, 1952), integrate-and-fire models (Brunel and Hakim, Fast global oscillations in networks of integrate-and-fire neurons with low firing rates, Neural Computation, 11:1621-71, 1999), or hybrids thereof (Breen et al., Hybrid integrate-and-fire model of a bursting neuron, Neural Computation, 15:2843-62, 2003). Some models based on lower-order systems like the second-order Fitzhugh-Nagumo (FN) relaxation oscillator (Fitzhugh, Impulses and physiological states in theoretical models of nerve membrane, Biophys J, 1:445-66, 1961) are formal mathematical reductions of the higher-order conductance-based models (Tuckwell and Rodriguez, Analytical and simulation results for stochastic Fitzhugh-Nagumo neurons and neural networks, J Comp Neurosci, 5:99-113, 1998), and therefore still associate with the dynamics of single neurons.

In the brain, complex rhythms and patterns of activity arise from ensemble interactions between groups of neurons. Relating specific network phenomena to individual cell-level connections or properties for such large, distributed networks is a daunting task. However, it is possible to replicate the activity of neuronal populations using cellular-level models with sufficiently generous computational resources and time. For example, Traub et al. (Model of the origin of rhythmic population oscillations in the hippocampal slice, Science, 243:1319-25, 1989) developed large-scale conductance and compartmental cell models for the CA1 and CA3 regions of the hippocampus, including one model of the CA3 that incorporated 9000 excitatory pyramidal cells and 900 inhibitory interneurons and were able to reproduce theta population rhythms. Others have focused on smaller networks, such as Kudela et al. (Changing excitation and inhibition in simulated neural networks: effects on induced bursting behavior, Biol Cybern, 88:276-85, 2003), who created a model of approximately 100 single-compartment neurons to explore the inhibitory-excitatory balance and its effect on synchronous population bursting.

Nevertheless, it is difficult to associate or duplicate high-level functionality such as cognition or memory with large networks comprised of many individual biophysically-representative neurons. An alternative approach to modeling neuronal populations involves treating a subpopulation or assembly of similarly behaving neurons as a fundamental network unit, in lieu of the single neuron, thereby limiting the demand on computational resources, improving efficiency, and reducing model parameters and structural complexity. From a modeling perspective, it makes sense to group neurons whose activities are coordinated or similar into assemblies that function as units within a larger network. The concept of neuronal functional blocks from a system perspective leads to a sensible means of organizing and parsing the brain with respect to understanding how aspects of cognition, memory, consciousness and pathology emerge from regional rhythms and connectivity (Buzsaki and Draguhn, Neuronal oscillations in cortical networks, Science, 304:1926-9, 2004).

Physiologically, neuronal assemblies are often observed to behave as oscillators with endogenous rhythmicity (Buzsaki et al., Hippocampal network patterns of activity in the mouse, Neurosci, 116:201-11, 2003), and their interactions are the result of ensemble cellular-level connections (Womelsdorf et al., Modulation of neuronal interactions through neuronal synchronization, Science, 316:1609-12, 2007). A network model of neuronal assemblies should therefore possess differential equations capable of generating oscillations, and include high-level connections representative of effective (ensemble) modalities of physiological coupling.

Wilson and Cowan (Excitatory and inhibitory interactions in localized populations of model neurons, Biophys J, 12:1-24, 1972) were amongst the first to derive coupled differential equations specifically catering to the dynamics of neuronal subpopulations. Their model is an abstraction of system level activity, in that the two dynamic variables, I(t) and E(t), pertain to the fraction of inhibitory and excitatory cells active at time t. Distributions were devised to account for thresholds and synapses, resulting in n-modal sigmoidal transfer functions characterizing the population response to excitation. In contrast, the lumped parameter model of Lopes da Silva (Model of brain rhythmic activity: the alpha-rhythm of the thalamus, Kybernetic, 15:27-37, 1974) generates outputs that are physiologically comparable to electroencephalographic (EEG) and local field recordings, and recent versions of the model have been used to investigate the dynamics of epileptic seizures (Wendling et al., Relevance of nonlinear lumped-parameter models in the analysis of depth-EEG epileptic signals, Biol Cybern, 83:367-78, 2000).

Such models are parametric and therefore require specification of a multitude of parameters that are typically measured from the biological system. This is especially true of cellular conductance-based models. Since the respective parameter values are not always accessible or observable, non-parametric methods, such as kernel models, are useful for describing certain dynamic or functional aspects of neural systems since kernel models do not require explicit knowledge of system parameters or internal structure. Instead, only the observed input(s) and output(s) to the system are needed to characterize the system behavior.

Kernel models of neural pathways have yielded insight into neural coding functionality and input-output dynamics; for example, how motor and sensory pathways code limb movement, direction, auditory and visual information (Gamble and DiCaprio, Nonspiking and spiking proprioceptors in the crab: white noise analysis of spiking CB-chordotonal organ afferents, J Neurophysiol, 89:1815-25, 2003). Input-output relationships in thalamocortical and hippocampal circuits have also been mapped using similar models (Frantseva et al., Changes in membrane and synaptic properties of thalamocortical circuitry caused by hydrogen peroxide, J Neurophysiol, 80:1317-26, 1998). The caveat, however, is that kernel-based models cannot reproduce the dynamics of generative systems that produce a time-varying output independent of any input, including intrinsic oscillations or rhythms (Marmarelis, Modeling methodology for nonlinear physiological systems, Ann Biomed Eng, 25:239-51, 1997), which can be classified as infinite memory phenomena.

It is therefore an object at least to provide a novel method of modeling time-dependent electrical dependent activity of a biological system, a novel cognitive rhythm generator, and a novel method of controlling or treating a seizure-like event.

SUMMARY OF THE INVENTION

According to one aspect there is provided a method of modeling time-dependent electrical activity of a biological system, the method comprising transforming an input through at least one dynamic mode to yield at least one modal output; processing the at least one modal output to yield at least one amplitude variable and at least one phase variable; and mapping the at least one amplitude variable and the at least one phase variable to an observable output.

According to another aspect there is provided a method of stimulating a biological system comprising transforming components of an input with respective neuronal modes to yield corresponding modal outputs; processing the modal outputs to yield amplitude and phrase variables; mapping the amplitude and phrase variables to an output; and stimulating the biological system with the output.

According to another aspect there is provided a cognitive rhythm generator comprising at least one dynamic mode for transforming an input to yield at least one modal output; at least one ring device processing the at least one modal output to yield at least one amplitude variable and at least one phase variable; and a mapper for mapping the at least one amplitude variable and the at least one phase variable to an observable output.

According to yet another aspect there is provided a method of controlling or treating a seizure-like event, the method comprising transforming an electrical input from neural tissue of a subject through at least one neuronal mode to yield at least one modal output; processing the at least one modal output to yield at least one amplitude variable and at least one phase variable; mapping the at least one amplitude variable and the at least one phase variable to an observable output;

and stimulating the neural tissue based upon the observable output, thereby controlling or treating the seizure-like event.

BRIEF DESCRIPTION OF THE DRAWINGS

Embodiments will now be described more fully with reference to the accompanying drawings in which:

FIGS. 4D to 4H show exemplary polar phase plots of the gamma spikes in relation to the theta phase for different gamma CRG mode settings;

FIGS. 14A to 14D show an example of a therapeutic CRG network containing 4 CRG units;

FIGS. 14E to 14F show traces experimentally recorded from a hippocampal slice preparation undergoing seizure-like activity;

DETAILED DESCRIPTION OF THE EMBODIMENTS

In the following, a model for neural coding is described. The model combines the methodologies of nonlinear systems modeling and coupled oscillators. These two approaches are hybridized in a construct referred to herein as a cognitive rhythm generator (CRG) to capture the diverse and sophisticated functionality and dynamic behaviour of the brain and to arrive at a general representation of neuronal assemblies and their coding functionality. The CRG is based on a generative model and enables quantitative representation of the intrinsic dynamics and input-output response characteristics of a nonlinear autonomous system. The CRG is useful in the modeling of time-dependent electrical activity of a biological system, such as for example a neuron or a region of the brain cortex. The CRG may be used to stimulate a biological system by connecting the CRG with the biological system to be stimulated through an appropriate electromechanical interface, such as a microelectrode array and supporting circuits.

Cognitive Rhythm Generator

Figure 1:
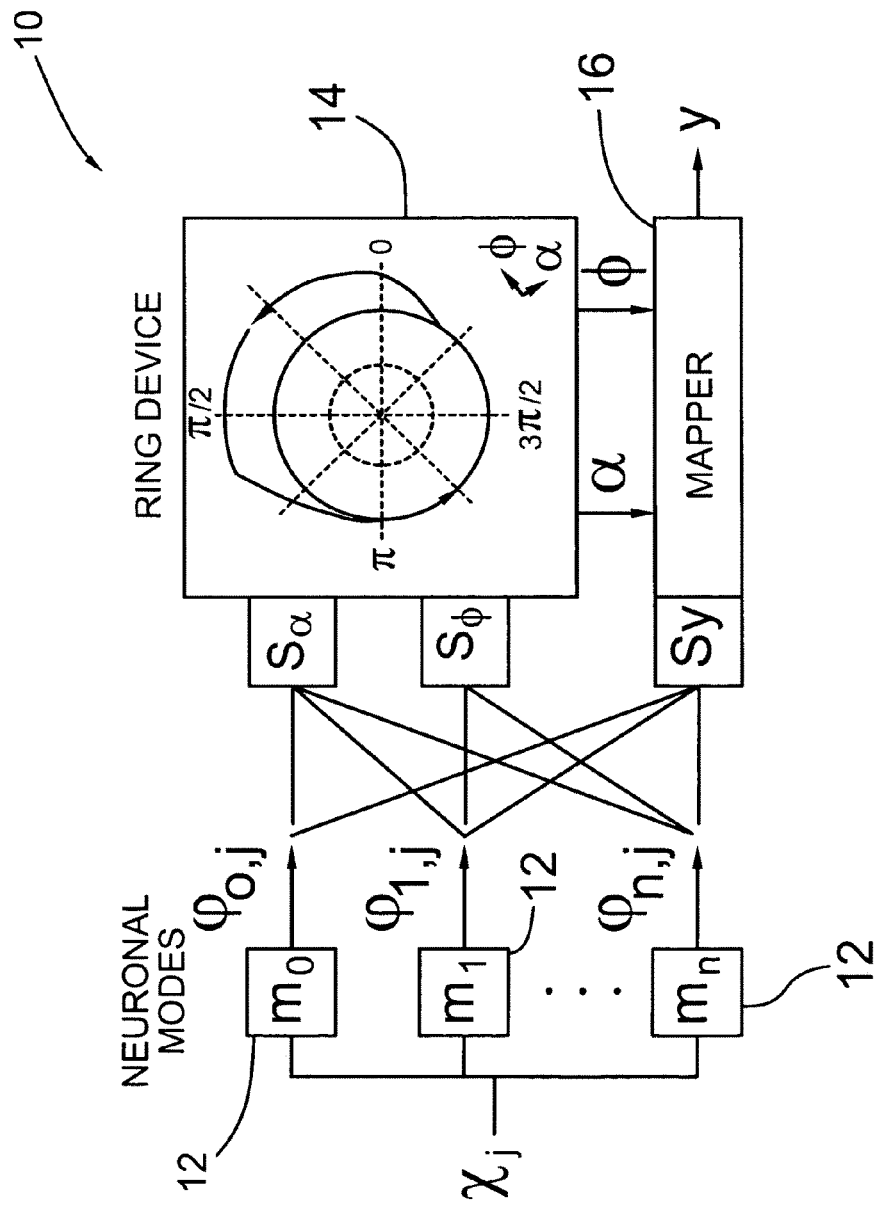
FIG. 1 is a schematic diagram of a cognitive rhythm generator (CRG)

Turning now to FIG. 1, a schematic diagram of one embodiment of a CRG is shown and is generally identified by reference numeral 10. The cognitive aspect of the CRG 10 is derived from a set or bank of neuronal modes 12 made up of individual neuronal modes $m_0 \ldots m_n$. The neuronal modes $m_0 \ldots m_n$ are projections of system kernels (Marmarelis, Modeling methodology for nonlinear physiological systems, Ann Biomed Eng, 25:239-51, 1997; Mitsis et al., Principal dynamic mode analysis of action potential firing in a spider mechanoreceptor, Biol Cybern, 96:113-27, 2007) and provide a functional representation of the input-output properties of the nonlinear system. In order for the CRG to clone or replicate the functional and dynamic behaviour of a biological system, the neuronal modes $m_0 \ldots m_n$ are firstly synthesized or measured, and then the parameters of the CRG are fitted or configured in a manner specific to the intended application.

The bank of neuronal modes 12 provides the medium through which the CRG 10 both perceives its environment and performs an initial transformation and decoding of an incoming signal or input $x_j$. Each of the neuronal modes $m_0 \ldots m_n$ is responsible for one component transformation of the input $x_j$ (e.g. integation, nth order differentiation, etc.). The neuronal modes $m_0 \ldots m_n$ yield modal outputs $\phi_{0,j} \ldots \phi_{n,j}$, which are mixed using mixing functions $S_a$, $S_\phi$, and $S_y$.

The rhythm generating aspect of the CRG 10 is derived from a ring device 14 (Winfree, The Geometry of Biological Time, $2^{nd}$ Ed., (New York: Springer-Verlag) 2001). The ring device 14 is a mathematical limit-cycle oscillator that generates a limit-cycle encoding dimensionless state amplitude $\alpha$ and phase φ variables from the modal outputs $\phi_{0,j} \ldots \phi_{n,j}$. In this way, the ring device 14 governs how the amplitude α and phase φ variables evolve with time. The amplitude α and phase φ variables are then mapped by a static nonlinearity, referred to as a mapper 16, to a physiologically-representative and physically observable output variable y.

The CRG 10 can account for phenomena such as directional selectivity, phase preference, and phase precession in neuronal systems. One particular example of this is phase locking and precession of gamma frequency activity in relation to the theta field oscillation, as observed in hippocampal place cell assemblies (Klausberger et al., Brain-state- and cell-type-specific firing of hippocampal interneurons in vivo, Nature, 421:844-8, 2003). Additive Gaussian white noise (GWN) is used to identify CRG kernels, from which principal dynamic modes (PDMs) are extracted for comparison with the neuronal modes $m_0 \ldots m_n$ in the model. The kernels provide information about input-output characteristics and explain the response variation of the CRG 10 associated with nonlinear modal mixing. Nonlinear modal mixing may be partly a consequence of network mechanisms such as disynaptic feedforward inhibition (DFI), because of the nonlinear frequency-dependent properties of circuits containing DFI (Mori et al., A frequency-dependent switch from inhibition to excitation in a hippocampal unitary circuit, Nature, 431:453-6, 2004). Such circuits are plausible candidates for deciphering upstream rate codes (e.g. originating from path-integration in the entorhinal cortex) to mediate downstream processes such as phase precession in the hippocampus.

The ionic channels and pumps embedded in the plasma membrane of excitable cells perform two major roles: the first is to generate and maintain a resting potential difference across the membrane; and the second, through voltage and ligand-gated channels, is to allow for abrupt, nonlinear changes in the potential. The resting level relates to the zero-order mode, which can be interpreted as a mean energy level when expressing the average potential of a neuronal assembly or population. Source potentials are smoothed and integrated by the resistive-capacitive (RC) properties of the membrane (Spruston and Johnston, Perforated patch-clamp analysis of the passive membrane properties of three classes of hippocampal neurons, J Neurophysiol, 67:508-29, 1992). Integrative transformations are also carried out at synapses and gap junctions, resulting in monophasic postsynaptic distributions for individual action potentials (Garcia-Perez et al., Synaptic integration in electrically coupled neurons, Biophys J, 86:646-55, 2004). Contributions from integrative mechanisms are responsible for shaping the first-order mode.

The polyphasic profile of higher-order modes originates from processes that further transform or combine monophasic source potentials. Evidence comes from the observation that higher-order modes tend to correspond to differentiated forms of the first-order mode. Local electric field communication between neurons is one way in which derivative transformations can occur (Vigmond et al., Mechanisms of electrical coupling between pyramidal cells, J Neurophysiol, 78:3107-16, 1997). Experimentally, the extracellular field recorded close to the cell surface has resembled either the first or second derivative of the intracellular potential (Spach et al., Extracellular potentials related to intracellular action potentials in the dog Purkinje system, Circ Res, 30:505-19, 1972). The arborization geometry and active properties of dendrites can elicit nonlinear transformations in the phasic profile of potentials (Gulledge et al., Synaptic integration in dendritic trees, J Neurobiol, 64:75-90, 2005). Neurons receiving multiple synaptic inputs from various sources can combine monophasic potentials in time and space to produce polyphasic postsynaptic potentials (Parker, Activity-dependent feedforward inhibition modulates synaptic transmission in a spinal locomotor network, J Neurosci, 23:11085-93, 2003) corresponding to the shape of higher-order modes. Network structures combine multiple communication modalities, enabling series and parallel transformations, as well as nonlinear transformations due to interplay of excitation and inhibition. Altogether, the repertoire of transformations is what gives rise to information processing in the nervous system, and the result is high-level functionality in the form of sensory perception, decision making, and cognition.

These biophysical processes are modeled indirectly by the CRG 10, which is different from other approaches such as conductance-based models that directly describe the action of ion channels and pumps, and require quantification of physical parameters such as capacitances and conductances. Biophysical approaches are well-suited to providing low-level mechanistic descriptions of action potential generation and electrical propagation, as well as modeling individual neurons and their interactions, but the difficulty lies in extrapolating high-level functionality from such models. Conversely, the CRG model yields nothing about the generation of action potentials or about ion channel physics, but rather offers insight as to how forms of neural coding and communication can be linked to specific cognitive functionality.

Multiple CRGs 10 may be coupled together to create a CRG network. CRG 10 coupling involves taking the output of the mapper 16 of a particular CRG 10 and feeding it to the bank of neuronal modes 12 of a second CRG 10. Such connections result in physiologically realistic output waveforms and rhythms of varying complexity. The topology or connectivity of such a CRG network is flexible and programmable in order to accommodate intended applications.

Figure 2A:
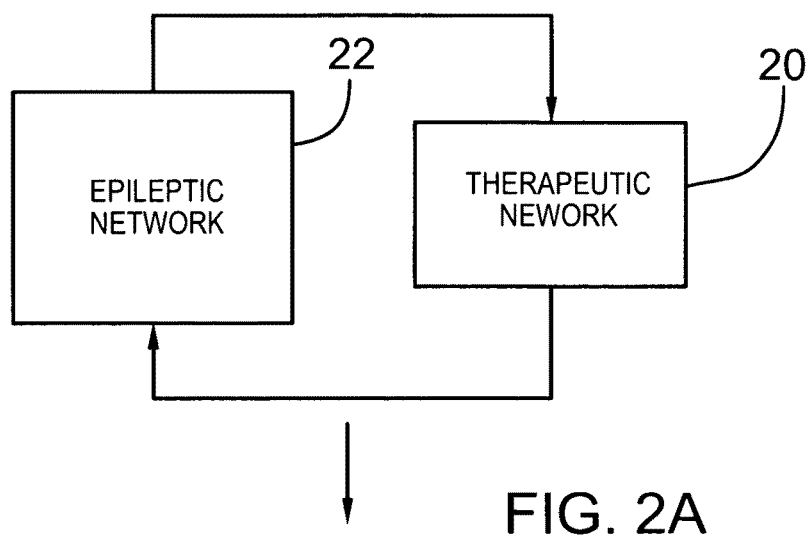
FIGS. 2A and 2B are schematic diagrams of a CRG network configured to implement seizure control.
Figure 2B:
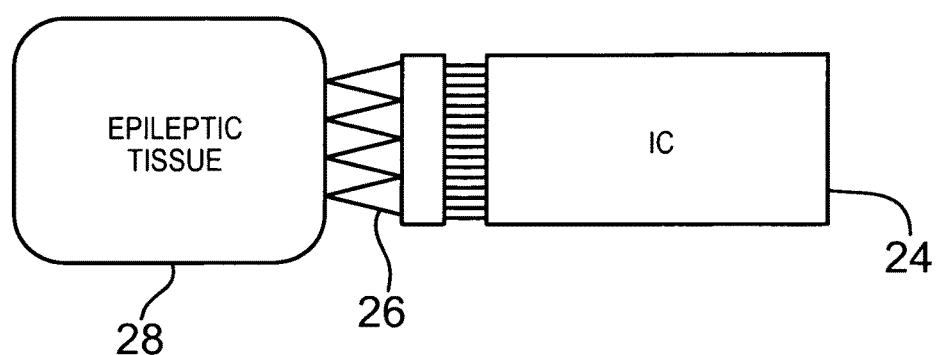

One such application is in medical therapy, such as, for example, to prevent, control, or treat seizures. To use CRG networks in a therapeutic capacity, the CRG networks are implemented in electronic hardware (e.g. very large scale integrated circuits (VLSI), application specific integrated circuits (ASIC), field programmable gate arrays (FPGAs), etc.) with a suitable interface for both stimulating and recording neural tissue simultaneously, such as, for example, a microelectrode array (MEA) or comparable technology. FIGS. 2A and 2B show a high-level schematic diagram of a CRG network suitable for use in seizure control. In FIG. 2A, feedback control using a therapeutic CRG network 20 interfacing with an epileptic network 22 is shown. Once a suitable therapeutic CRG network 20 has been tested and simulated in silico, the CRG network may be implemented in hardware on an integrated circuit (IC) 24 with a suitable interface such as a MEMS electrode array 26 to simultaneously record and stimulate epileptic tissue 28 as shown in FIG. 2B. Hardware versions of neural models have been developed for other applications not related to therapy and their implementation is fairly straightforward using off-the-shelf electronic components. Programmable logic devices or controllers may be used, as these would enable internal network parameters and connectivity to be updated or customized to a specific patient. If implanted, the size and power dissipation of the CRG network would be important design considerations.

The systems approach of the CRG model is therefore realized through mathematical analogy of the transformative and generative biophysical processes underscoring neural information processing. Integrative and derivative transformations are carried out by transfer functions represented by neuronal modes. Rhythms are encoded by ring devices operating on limit-cycle dynamics. Series and parallel transformations are achieved by mixing mode outputs, and this can be done in a linear or nonlinear manner, allowing for unparalleled flexibility in coding.

Neuronal Modes

As mentioned above, the input $x_j$ to the CRG 10 is processed through the bank of neuronal modes 12. Each neuronal mode $m_0 \ldots m_n$ performs a unique transformation of the input $x_j$ that is dependent on the neuronal mode's $m_0 \ldots m_n$ shape and decay rate. The modal outputs $\phi_{0,j} \ldots \phi_{n,j}$ at time t are obtained by convolution of the jth input, $x_j$, with the kth mode, $m_k$ according to Equation (1) below:

$$\varphi_{k,j}(t) = \int_0^\infty m_k(\tau) \cdot x_j(t-\tau) d\tau. \quad (1)$$

Experimentally, neuronal modes $m_0 \ldots m_n$ are extracted from an eigen-decomposition of the measured Volterra or Wiener system kernels that encode the dynamic response of the biological system through the respective Volterra or Wiener functional series (Marmarelis, Modeling methodology for nonlinear physiological systems, Ann Biomed Eng, 25:239-51, 1997). A known method for estimating the kernels is the Laguerre Expansion Technique (LET), which expands the kernels over an alternative basis of Laguerre functions (Marmarelis, Identification of nonlinear biological systems using Laguerre expansions of kernels, Ann Biomed, Eng, 21:573-89, 1993). A set of principal dynamic modes (PDMs) characterizing the system may be computed using the method described by Marmarelis (Modeling methodology for nonlinear physiological systems, Ann Biomed Eng, 25:239-51, 1997). In theory, because determination of the dynamic modes depends on a black-box approach, whereby only the system inputs and outputs need to be explicitly known, the functional behaviour of arbitrary neuronal systems ranging from the individual neuron to large populations can be effectively modelled by the CRG 10. Only the genre of stimulation and recording will differ in a case-dependent manner (e.g. field electrodes to record and stimulate neuronal populations versus patch electrodes for individual neurons or local circuits).

Although neuronal modes $m_0 \ldots m_n$ and their associated kernels assume a variety of forms, they possess traits that can be related back to their functionality. One of the most significant traits for the application of neural coding purposes is the number of zero-crossing phases, which indicates whether the neuronal mode $m_0 \ldots m_n$ will act as an integrator or differentiator, or a combination of both. A monophasic neuronal mode exhibits low-pass characteristics, serves to accumulate signal power and acts as an integrator. A biphasic neuronal mode has band-pass characteristics and acts as a first-order differentiator. An n-phasic neuronal mode approximates (n−1) order differentiators. Neuronal modes with asymmetric phases can exhibit a mixture of integrator and differentiator characteristics, depending on the size, polarity and ordering of the phases relative to one another.

Figure 3A:
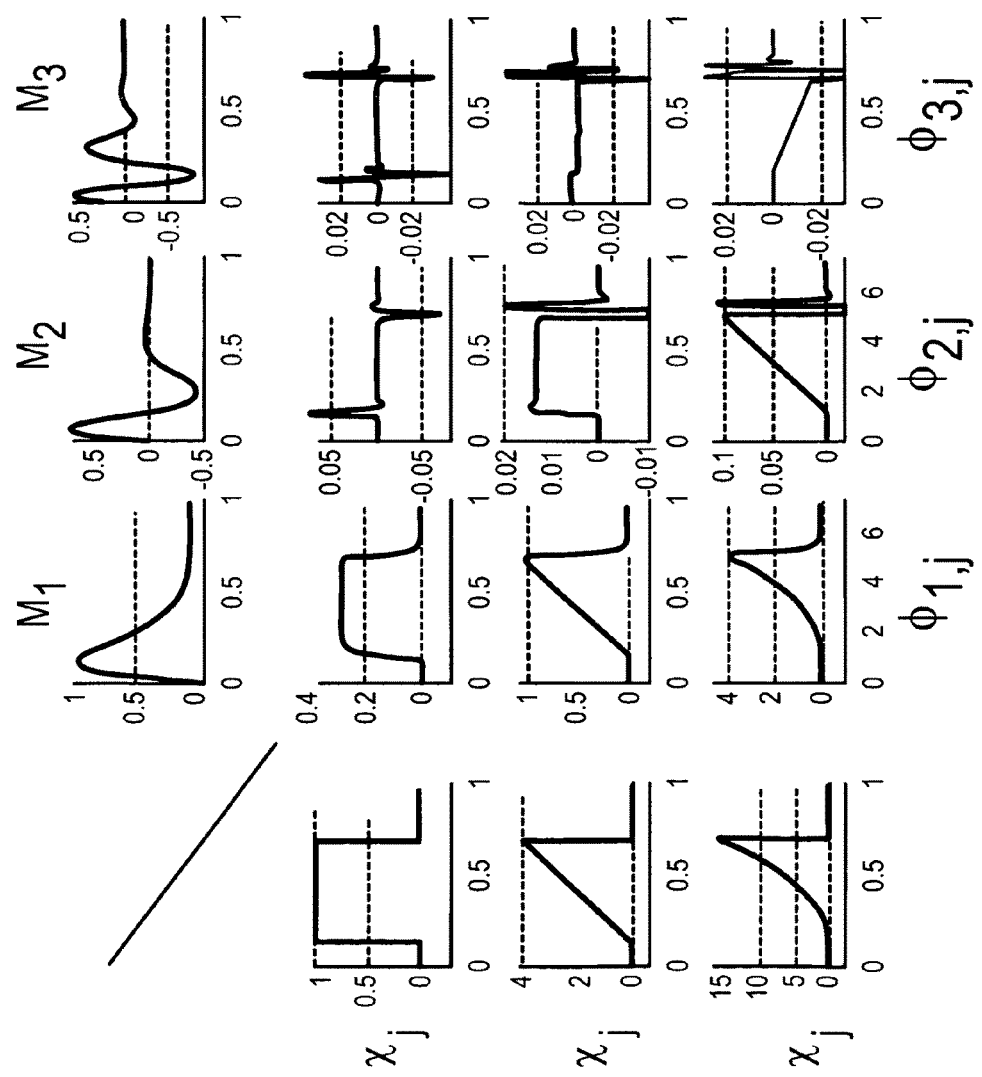
FIG. 3A is a response matrix of the modal outputs of the CRG of FIG. 1.

FIG. 3A shows an exemplary response matrix showing modal outputs $\phi_{0,j} \ldots \phi_{n,j}$ for three types of inputs $x_j$: a step function, a linear ramp, and a quadratic ramp; and for three types of neuronal modes $m_0, m_1, m_2$: monophasic, biphasic and triphasic. The neuronal modes were synthesized analytically using formula (2) below:

$$m_k(t) = a_k t \exp(1-a_k t)\{\cos((k-1)a_k t) + b_k\} \quad (2)$$

where $a_k$ is a constant controlling mode decay rate, $b_k$ is an offset term, and $k \geq 1$.

In this example, $a_k = a$ for all k, where a is set depending on model requirements. In this arrangement, 1/a is also the time-delay to the peak of the monophasic neuronal mode for k=1. For the examples in FIG. 3A, $a_1 = a_2 = a_3 = a = 10/s$; $b_1 = b_2 = 0$, and $b_3 = 0.12$.

As can be seen, the monophasic neuronal mode $m_1$ (k=1) acts as an integrator, and yields outputs $\phi_{1,j}$ that follow the rise and fall of the inputs $x_j$. Therefore, the monophasic neuronal mode m, codes for displacement. The biphasic neuronal mode $m_2$ (k=2) produces outputs $\phi_{2,j}$ that mimic the first derivative of the inputs $x_j$. The biphasic neuronal mode $m_2$ captures the polarity of the step edges (up=positive, down=negative), and responds to the linear ramp input with a constant offset, and to the quadratic ramp input with a linearly increasing output $\phi_{2,j}$. The linear ramp input $x_j$ can be interpreted in terms of constant velocity, and the quadratic ramp input $x_j$ can be interpreted in terms of constant acceleration. Therefore, the biphasic neuronal mode $m_2$ codes for velocity. The triphasic neuronal mode $m_3$ (k=3) does not respond to the step input or the linear ramp input, but only to the quadratic ramp input. The triphasic neuronal mode $m_3$ also exhibits predominantly biphasic responses to step edges, with phasic polarity switching along the inflection of the edge. Hence, the triphasic neuronal mode $m_3$ codes for acceleration. Because the phases of the triphasic neuronal mode $m_3$ are asymmetric, it retains a small velocity component, which is why the response to the quadratic ramp input is inclined. The zero-order neuronal mode $m_0$ (k=0) is a scalar term, and the output is a scaled version of the input (not shown). The CRG 10 definition of the zero-order neuronal mode $m_0$ differs from its conventional definition as an average system response that is independent of the input $x_j$.

The properties of neuronal modes, including their shape and decay length, are inherited from the measured system kernels. This means that the dynamic response of a biological system can be adequately captured in the CRG model by extracting the principal dynamic modes of the system, and substituting them directly into the bank of neuronal modes 12, as seen in FIG. 1, in place of the synthesized modes of Equation (2).

Figure 3B:
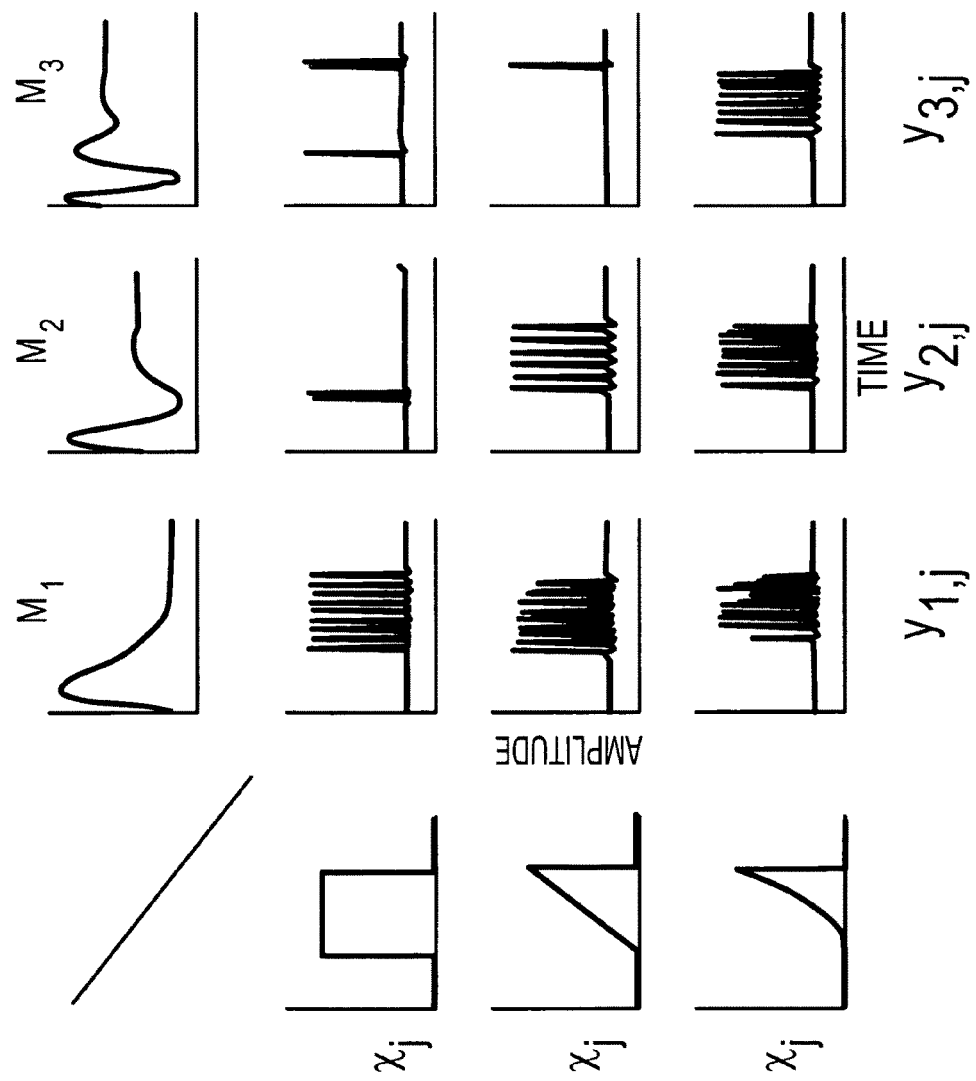
FIG. 3B shows the rate-varying spike output from the mapper as it corresponds to the input mode pairings of FIG. 3A.

Treating kernels and modes in the context of integration and differentiation allows for explicit association of form to function, as is demonstrated in the case of spatial coding of displacement, velocity and acceleration. Gamble and DiCaprio (Nonspiking and spiking proprioceptors in the crab: white noise analysis of spiking CB-chordotonal organ afferents, J Neurophysiol 89:1815-25, 2003) measured the first and second-order Wiener kernels from crab limb proprioceptive afferents, and discovered four separate response classes corresponding to position, mixed position-velocity, velocity and acceleration. The position-sensitive afferents had predominantly monophasic kernel profiles; the velocity-sensitive first-order kernels were biphasic; the acceleration first-order kernels were triphasic; and the position-velocity afferents displayed asymmetric biphasic first-order kernels. These results are consistent with the CRG classification of modes and modal responses, as shown in FIGS. 3A and 3B.

Similar results were obtained from spider mechanoreceptors and locust chordotonal organs (French and Marmarelis, Nonlinear analysis of neuronal systems, Modern Techniques in Neuroscience Research, pp. 627-640, 1999), as well as from catfish retina (Naka et al., Generation and transformation of second-order nonlinearity in catfish retina, Ann Biomed Eng, 16:53-64, 1988), blowfly optic lobe in response to modulated visual stimuli (Kondoh et al., A neural computation of motion in the fly visual system: quadratic nonlinearity of responses induced by picrotoxin in the HS and CH cells, J Neurophysiol, 74:2665-84, 1995), and from vestibular neurons of the macaque monkey in response to rotational velocity and acceleration (Klam and Graf, Vestibular response kinematics in posterior parietal cortex neurons of macaque monkeys, Eur J Neurosci, 18:995-1010, 2003), highlighting the universality in the nature of these coding relationships.

Modal Mixing

The modal outputs $\phi_{0,j} \ldots \phi_{n,j}$ are internal variables to the CRG 10 and as mentioned above are fed via missing functions $S_\alpha$, $S_\phi$ and $S_y$ to the ring device 14 to generate a limit cycle encoding the dimensionless state amplitude $\alpha$ and phase $\phi$. The mixing functions $S_\alpha$ and $S_\phi$ scale and combine the modal outputs $\phi_{0,j} \ldots \phi_{n,j}$ so that they can modulate the rates of change of the amplitude $\alpha$ and phase $\phi$, variables respectively. The mixing function $S_y$ defines how the modal contributions are combined at the observable output y of the CRG 10 as seen in FIG. 1.

The manner in which modal mixing is defined depends on the requirements of the model and in general it can be any arbitrary function. In this example, the mixing functions take the form of a linear combination (unless otherwise specified) according to Equation (3) below:

$$S_u = \varepsilon_u \sum_k \sum_j \mu_{k,j} \varphi_{k,j} \qquad (3)$$

where $\mu_{k,j}$ is the coefficient (gain) of the kth modal output pertaining to the jth input, and $\varepsilon_u$ is the channel gain (for $u=\{\alpha, \phi, y\}$). Exemplary channel gains are normalized as shown in Table 1 below.

TABLE 1

| Parameter/Variable | Default Value[a] | | Equations |
|---|---|---|---|
| | $\theta$ | $\gamma$ | |
| Channel gain | $\varepsilon_\alpha$ | $10^2/\sigma$ | (3) |
| | $\varepsilon_\phi$ | $10^3/\sigma$ | |
| | $\varepsilon_y$ | 0 | |
| Channel normalization factor[b] | $\sigma$ | $\sqrt{\frac{1}{2\pi}\int_0^{2\pi} [W(u)]^2 \, du}$ | |
| Refractory function | $R_\alpha(\phi)$ | $c_1 = 1, c_2 = -\infty$ | (5a), (5b), (6) |
| | $R_\phi(\phi)$ | $c_1 = 5, c_2 = 9\pi/25$ | (4), (6) |
| Labile threshold function | $v(S_\alpha)$ | $c_1 = 30, c_2 =$ model dependent[c] | (5b), (6) |
| Intrinsic frequency | $\omega$ | $12\pi$ rad/s   $40\pi$ rad/s | (4) |
| Rate constant | $k_\alpha$ | $\omega_\theta$   $10^3/s$ | (5a), (5b) |

[a]The stated value applies for the exemplary application of phase coding, unless otherwise specified. In general, CRG model parameters will depend on the intended application.
[b]Equal to the root-mean-square value of the intrinsic output waveform, W, which is normalized in phase over the interval (0, $2\pi$). The theta intrinsic waveform was synthesized, while the gamma spike waveform was obtained from a whole-cell recording of a CA1 interneuron ($\sigma_\gamma$ = 6.68 mV).
[c]The activation threshold ($c_2$) was set according to model requirements.

Ring Device

To encode neural rhythms, the ring device 14 employs a clock, and a labile clock. The labile clock, as its name suggests, requires a suprathreshold stimulus to produce an observable output, hence its activity is labile. The clock, conversely, generates an omnipresent rhythmic output even in the absence of any input. The two clocks are used to model neuronal assemblies, because some assemblies are quiescent unless excited by neighbouring populations or stimulated extrinsically. In contrast, other neuronal assemblies exhibit spontaneous rhythmic activity. Further specifies concerning the properties and dynamics of the ring device 14 are discussed in Zalay and Bardakjian (Mapped clock oscillators as ring devices and their application to neuronal electrical rhythms, IEEE Trans Neural Syst Rehabil Eng, 16:233-44, 2008), the contents of which are incorporated herein by reference.

The ring device 14 equation governing the rate of change of the phase (in radians) is the same for the clock and for the labile clock, and is expressed according to Equation (4) below as:

$$\frac{d\phi}{dt} = \omega(1 + R_\phi(\phi)S_\phi) \qquad (4)$$

where $\omega$ is the intrinsic frequency (rad/s) and $R_\phi$ is a refractory function.

The range of $\phi$ is constrained to the interval (0, $2\pi$) and covers one complete cycle. Phase advance is also limited to being positive or zero. The refractory function $R_\phi$ prevents the ring device 14 from responding to phase stimulation early in its cycle, during the refractory period.

The rate of change of amplitude for the clock and labile clock are given by the Equations 5a and 5b respectively:

$$\frac{d\alpha}{dt} = \begin{cases} k_\alpha \alpha(1 + R_\alpha(\phi)S_\alpha - \alpha^2), & \text{clock} \quad (5a) \\ k_\alpha \alpha^{1/3}(R_\alpha(\phi)v(S_\alpha) - \alpha), & \text{labile} \quad (5b) \end{cases}$$

where $k_\alpha$ is a rate constant (1/s), $R_\alpha$ is a refractory function, and $v$ is a threshold function controlling activation of the labile clock.

To preserve the physical interpretation of limit cycle amplitude, $\alpha$ does not assume negative values. Converting the dynamics of the CRG 10 from those of a clock to a labile clock, for example, is done by substituting Equation (5b) for Equation (5a). The refractory functions $R_\phi$, $R_\alpha$, and the threshold function $v$ are all sigmoids of the form:

$$s(u) = \frac{1}{1 + \exp(-c_1(u - c_2))} \qquad (6)$$

where $c_1$ and $c_2$ are constants defined in Table 1 for each function.

The dynamics of the ring device 14 can be modulated by the modal outputs $\phi_{0,j} \ldots \phi_{n,j}$ and input $x_j$. Because of the presence of the ring device 14, the CRG 10 is a generative model able to produce outputs in the absence of inputs under select modes of operation. As such, the CRG 10 may be used as a stimulator when implemented in electronic hardware.

CRG Output

The instantaneous amplitude $\alpha$ and phase $\phi$ variables are mapped to the observable output variable y of the CRG 10 by the mapper 16. The mapper 16 assumes the following format according to Equation (7) below:

$$y = S_y + \alpha W(\phi) \qquad (7)$$

where $S_y$ is the mixing function to the mapper 16 in Equation (3), and W is the intrinsic output waveform of the CRG, which is normalized in phase over the interval 0 to $2\pi$. In its most general form, the mapper 16 is defined by an arbitrary function of the modal and ring device outputs.

For a dynamic ring device 14, Equations (4) to (5b) are solved using Gear's method of order 2, suitable for stiff systems of nonlinear differential equations (Gear, The automatic integration of ordinary differential equations, Comm ACM, 14:176-9, 1971). The modal outputs $\phi_{0,j} \ldots \phi_{n,j}$ are computed iteratively at each step of the solution by approximating Equation (1) as a discrete sum over the time-increments taken by the solver. FIG. 3B summarizes the responses of a labile CRG 10 to step, ramp and quadratic ramp inputs $x_j$ through first-order, second-order, and third-order neuronal modes $m_1$, $m_2$, and $m_3$, respectively, following the example of FIG. 3A. Activation thresholds are scaled accordingly for the different cases. The mixing functions are defined as follows: $S_\alpha=0.1\cdot S_\phi$, $S_\phi=\epsilon_\alpha(\mu_1\phi_1+\mu_2\phi_2+\mu_3\phi_3)$ and $S_y=0$, with mode coefficients of 1, 0, 0 (first column), 0, 1, 0 (second column) and 0, 0, -1 (third column), respectively, to obtain the independent outputs $y_{1,j}$, $y_{2,j}$, and $y_{3,j}$.

Mapper

The Laguerre Expansion Technique (LET) (Marmarelis, Identification of nonlinear biological systems using Laguerre expansions of kernels, Ann Biomed Eng, 21:573-89, 1993) is applied to estimate the first and second-order kernels from the responses of the CRG model to subthreshold Gaussian white noise stimulation. A modified version of the MATLAB™ toolbox for LET (The MathWorks, Natick, Mass.), derived from the software package LYSIS 7.1 from the Biomedical Simulations Resource of the University of Southern California, is used to compute the kernel estimates. With LET, the sampled system response, y, is fitted to a multinomial expansion on a basis of discrete Laguerre functions according to:

$$y(k) = c_0 + \sum_j c_1(j)u_j(k) + \sum_{j_1}\sum_{j_2} c_2(j_1, j_2)u_{j_1}(k)u_{j_2}(k) + \ldots \quad (8)$$

where $c_n$ are the nth-order expansion coefficients, determined by least-squares regression, and $u_j$ is a discrete convolution of the input x, with the jth Laguerre function, $L_j$:

$$u_j(k) = \sum_r L_j(r)x(k-r) \quad (9)$$

over integer time lags $r=0, 1, 2, \ldots, M-1$. The N discrete Laguerre functions used in the expansion ($j=0, 1, 2, \ldots, N-1$) are constructed from the expression (Ogura 1985):

$$L_j(r) = \sqrt{\beta^{r-j}(1-\beta)} \cdot \sum_{n=0}^{j} (-1)^n \binom{r}{n}\binom{j}{n}\beta^{j-n}(1-\beta)^n. \quad (10)$$

Parameter $0<\beta<1$ controls the decay rate of Equation (10), and is selected to adequately span the memory of the response. Once the coefficients in Equation (8) are known, the zero, first and second-order kernels are given by:

$$q_0 = c_0 \quad (11a)$$

$$q_1(r) = \sum_j c_1(j)L_j(r) \quad (11b)$$

$$q_2(r_1, r_2) = \sum_{j_1}\sum_{j_2} c_2(j_1, j_2)L_{j_1}(r_1)L_{j_2}(r_2). \quad (11c)$$

The accuracy of the kernel estimates is gauged by the percentage mean-squared error between the predicted output of the kernel model, Equation (8) versus the response of the original system $y_o$ to a stimulus different than the one used to fit the coefficients (French and Marmarelis, Nonlinear analysis of neuronal systems, Modern Techniques in Neuroscience Research, pp. 627-640, 1999):

$$\text{error} = \frac{\overline{(y(k) - y_o(k))^2}}{\overline{y_o^2(k)} - [\overline{y_o(k)}]^2} \times 100\% \quad (12)$$

where the bar signifies average value over all k samples.

Modes associated with the kernels in Equations (11a) to (11e) can be isolated by eigen-decomposition of the (M+1)×(M+1) matrix Q of kernel values (Mitsis et al., Principal dynamic mode analysis of action potential firing in a spider mechanoreceptor, Biol Cybern, 96:113-27, 2007):

$$Q = \begin{bmatrix} q_0 & \frac{1}{2}q_1^T \\ \frac{1}{2}q_1 & q_2 \end{bmatrix} \quad (13)$$

where superscript T denotes the transpose, $q_1$ is an M×1 row vector of first-order kernel values, and $q_2$ is the M×M second-order kernel.

The eigenvectors of Equation (13) associated with the largest eigenvalues in terms of magnitude contribute the most to the system response, and are chosen to construct impulse responses constituting the principal dynamic modes (PDMs) of the system (Marmarelis, Modeling methodology for nonlinear physiological systems, Ann Biomed Eng, 25:239-51, 1997):

$$\hat{m}_i(r) = \sum_{j=1}^{M} \xi_{i,j}\delta(r-j+1) \quad (14)$$

where, $\xi_{i,j}$ is the jth element ($j=0, 1, \ldots M$) of the ith significant eigenvector, and $\delta$ is the discrete Kronecker delta. The significance level $\chi$ is defined whereby the ith eigenvalue $\eta_i$ is selected if it meets the following criterion:

$$\frac{|\eta_i|}{\sum_j |\eta_j|} > \chi. \quad (15)$$

EXAMPLES

Example 1

Phase Selectivity

Figure 4A:
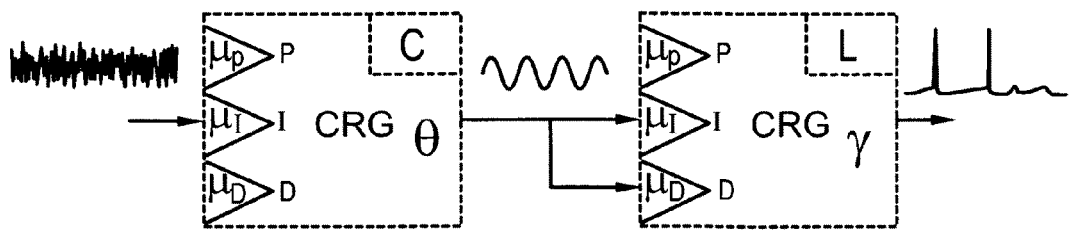
FIG. 4A shows an exemplary 2-CRG network model.

Event timing or spatial relationships between an organism and its environment, or with respect to the organism itself (e.g. idiothetic self-cues), may reflect natural phase preferences in the rhythmic firing of neuronal ensembles. FIG. 4A shows an example of a CRG network comprising two (2) CRGs applied to obtain a functional-level description of neural phase coding through the combined action of neuronal modes and ring devices. The CRG network of FIG. 4A in this example is suitable for hippocampal theta coding using a clock (theta) CRG generating the population theta rhythm coupled to a labile (gamma) CRG representing local assembly-specific gamma activity. Here, three modes are indicated: P for a proportional zero-order mode; I for an integrating (monophasic) first-order mode; and D for a differentiating (biphasic) second-order mode. In this example, the output of the clock CRG represents the population theta oscillation, but in general the phase-varying signal can be modeled after any source because the coding aspects are similar, regardless of whether the phenomenon being considered is a sinusoidal voltage oscillation, a moving visual stimulus or shifting head orientation. Gaussian-distributed noise of mean zero and variance 2 was added through the clock CRG's integrating mode to introduce random variations in the theta rhythm (θ: $\mu_P=0$; $\mu_1=1$; $\mu_D=0$).

Figure 4B:
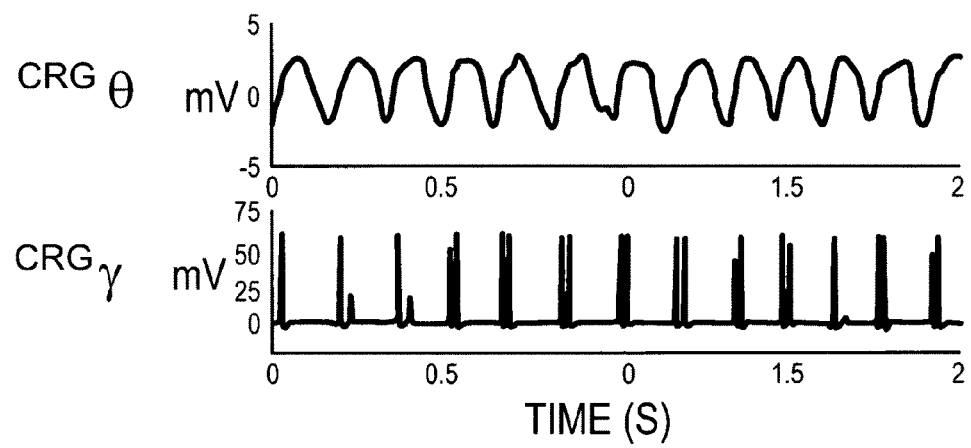
FIG. 4B shows an exemplary time series of the theta and gamma CRGs of FIG. 4A.
Figure 4C:
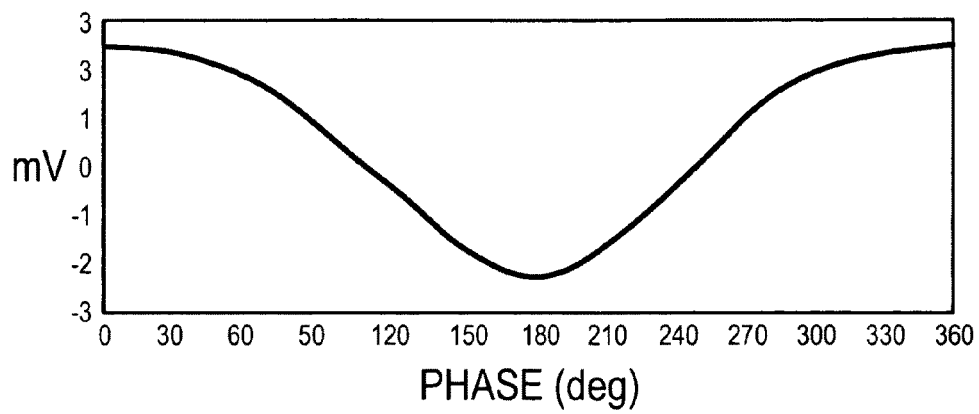
FIG. 4C shows an exemplary intrinsic output waveform of the theta CRG of FIG. 4A as a function of phase.

Example time series of the phase-locked CRGs are presented in FIG. 4B, using γ: $\mu_P=0$, $\mu_1=0$, and $\mu_D=0.5$ for the labile CRG. The phase-angle mapping of the theta waveform is shown in FIG. 4C. Polar plots of the resultant gamma CRG spike activity as a function of theta phase are presented for different modal contributions in FIGS. 4D to 4H. Both mode polarity and shape dictate the phase preference of the gamma activity in relation to the theta rhythm (positive monophasic=crest; negative monophasic=trough; positive biphasic=rising edge; negative biphasic=the descending edge; combinations code in between phases). The time-delay 1/a introduced by the modes of Equation (2), is corrected in the computation of the results (a=80/s, for both the clock and labile CRGs). There is a slight bias with respect to spike phases toward the counter-clockwise direction, as is evident in the polar plots, because the secondary and tertiary spikes (if present) occur later in phase than the initial spike immediately following activation.

Mode functionality enables temporal coding, whereby neurons coordinate their activity with respect to each other and with respect to time. For example, in the presence of population rhythmic oscillations, some neuronal groups in the population have a tendency to fire on the crest, trough or rising/descending edge of the oscillation, depending on their phase preference, as shown. Selective phase locking is observed in cortical and hippocampal regions during emergence of sustained low-amplitude field rhythms (Molle et al., Hippocampal sharp wave-ripples linked to slow oscillations in rat slow-wave sleep, J Neurophysiol, 96:62-70). System identification of these regions show kernel and modal forms characteristic of integrative and derivative transformations (Naylor, Changes in nonlinear signal processing in rat hippocampus associated with loss of paired-pulse inhibition or epileptogenesis, Epilepsia, 43 Suppl 5:188-93, 2002). Moreover, shifting phase preference, which is observed during theta phase precession, can serve to update temporal patterns of activity in neuronal ensembles, which may be useful for coding location or events. Because the activity shifts to earlier phases in the theta cycle—such as in the case of a foraging animal traversing a place field—theta precession is hypothesized to encode sequential aspects of spatial or episodic experience (Buzsaki, Hippocampal network patterns of activity in the mouse, Hippocampus, 15:827-40, 2005). The consolidation of those learned experiences occurs during sleep when the sequences are replayed in time-compressed form, activating mechanisms of synaptic plasticity (Lee and Wilson, Memory of sequential experience in the hippocampus during slow wave sleep, Neuron, 36:1183-94, 2002). In an animal model of medial temporal lobe epilepsy, impaired precession and temporal compression resulted in poor spatial memory and navigation abilities (Lenck-Santini and Holmes, Altered phase precession and compression of temporal sequences by place cells in epileptic rats, J Neurosci, 28:5053-62, 2008).

Example 2

Polarization-Dependent Precession

Depolarizing or hyperpolarizing current injections have been known to induce phase shifts in hippocampal network neurons in the presence of theta oscillations (Bland et al., Relationship between membrane potential oscillations and rhythmic discharges in identified hippocampal theta-related cells, J Neurophysiol, 88:3046-66, 2002). In a study by Kamondi et al. (Theta oscillations in somata and dendrites of hippocampal pyramidal cells in vivo: activity-dependent phase-precession of action potentials, Hioppocampus, 8:244-61, 1998), a sinusoidal theta-frequency current was injected into rat CA1 pyramidal place cells in vivo, atop a depolarizing bias current. While the burst-firing of the cells displayed preference for the rising edge of the sinusoidal stimulus, leading spikes shifted to earlier phases of the stimulus as the level of depolarization was increased, and bursts also intensified in duration and firing density.

This polarization-dependent phase precession experiment can be reproduced in a single CRG 10 by introducing a constant offset through the CRG's proportional mode, then injecting a sinusoidal current through its higher-order modes, with the choice of those modes falling to underlying phase preference. The labile CRG (from FIG. 4A) is selected as the test unit; its decay constant is adjusted to a=40/s, and a 5 Hz sinusoidal stimulus, $v_x=\sin(2\pi 5t)$, is delivered through its differentiating mode ($\mu_D=1.3$). Polarization offsets of −35, −25, −15, and −10 mV from the zero level are imposed through the proportional mode, with $\mu_P=1$ ($\mu_1=0$). The channel gains are both set so that $S_\alpha=S_\phi$. For clarity, the modal outputs are not shown in the mapper 16 output ($S_y=0$), only suprathreshold spikes.

Figure 5A:
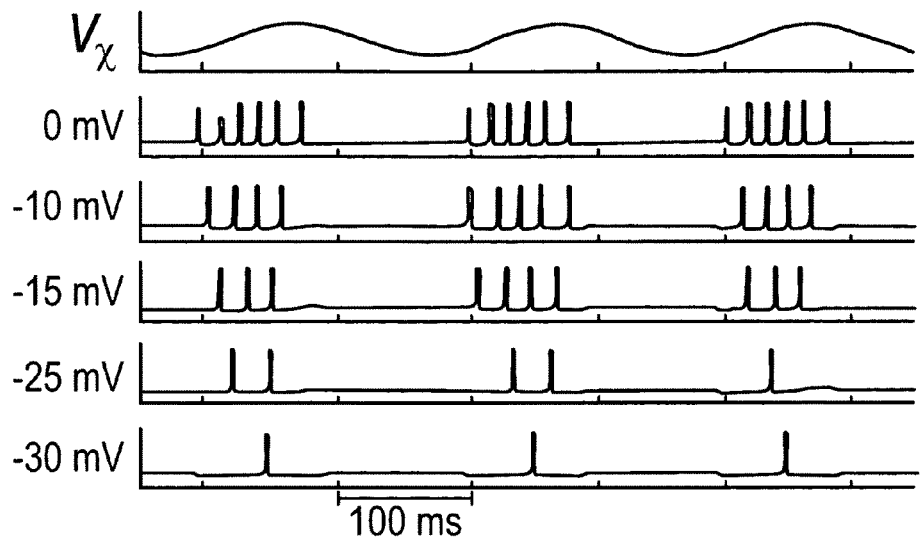
FIG. 5A shows exemplary phase shifts produced by changing polarization levels.
Figure 5B:
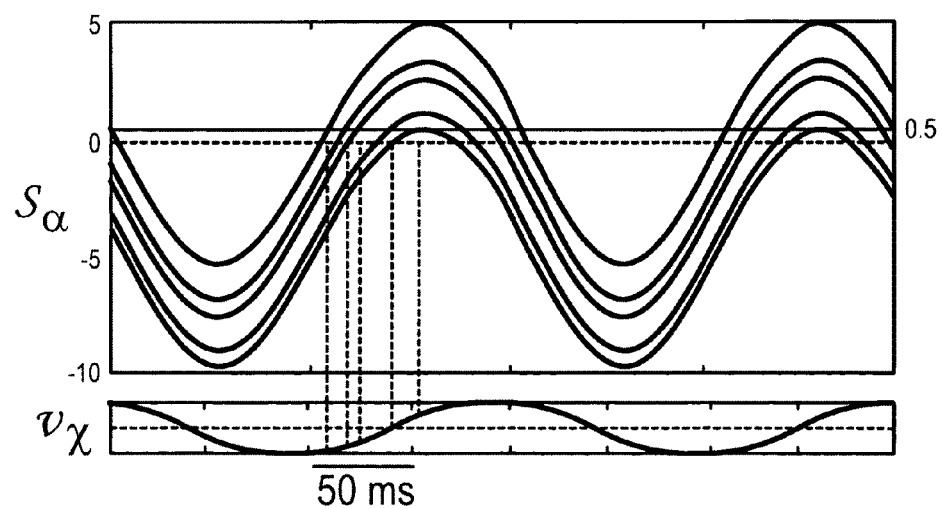
FIG. 5B shows the mechanism for polarization dependent phase precession.

The results of the model are in agreement with experimental observations, in that the gamma spiking of the CRG shifted toward earlier phases of the sinusoidal input as the unit is incrementally depolarized as shown in FIG. 5A. The model also suggests a mechanism to account for polarization-dependent phase shifts as shown in FIG. 5B, namely, that the offset determines the points of intersection of the unit's time-varying excitation level (given by $S_\alpha$) with the threshold, which is 0.5 in this example. The greater the level of depolarization, the earlier in time the rising edge intersection occurs, and hence the earlier the phase of the lead spike. The peak excitation occurs along the rising edge of the sinusoid as a result of the phase preference imparted by the biphasic second-order mode. Another feature corroborating this model is that the more depolarized states have larger numbers of spikes per burst. As depolarization is increased, the sinusoidal excitation level remains above threshold for longer, thereby accounting for earlier appearance and longer duration of the gamma-frequency bursts. The increase in burst size with depolarization is also seen experimentally, without significant difference in the underlying phase preference.

Example 3

Precession by Variation in Modal Character

Theta phase precession in the navigating rat occurs when neurons in an activated place field fire consecutively at earlier phases of the underlying theta field oscillation. The degree of precession is observed to be correlated to the distance traversed in a given place field, not the time the animal spends in the place field (O'Keefe and Recce, Phase relationship between hippocampal place units and the EEG theta rhythm, Hippocampus, 3:317-30, 1993). The rate of precession depends on the size of the place field and how quickly the animal moves through it. Smaller place fields correlate with faster precession rates than larger ones. For the same place field, the precession slope will be steeper for a quicker animal than a slower moving one, presumably due to the greater distance covered per unit time (Geisler et al., Hippocampal place cell assemblies are speed-controlled oscillators, PNAS, 104:8149-54, 2007). While the extent of the total phase shift may vary from one place field to another, it typically does not exceed 360 degrees, or one theta cycle (O'Keefe and Recce, Phase relationship between hippocampal place units and the EEG theta rhythm, Hippocampus, 3:317-30, 1993). The activity of hippocampal place cells can be modulated by external sensory cues, such as visual landmarks, which can reorient the cognitive map, yet complete darkness or lack of external cues do not appear to hinder phase precession in relation to the animal's movement (Moser et al., A test of the reverberatory activity hypothesis for hippocampal 'place' cells, Neuroscience, 130:519-26, 2005), suggesting that an internal path-integration mechanism or internal self-cues are responsible for orchestrating precession (Hafting et al., Microstructure of a spatial map in the entorhinal cortex, Nature, 436:801-6, 2005).

Figure 6A:
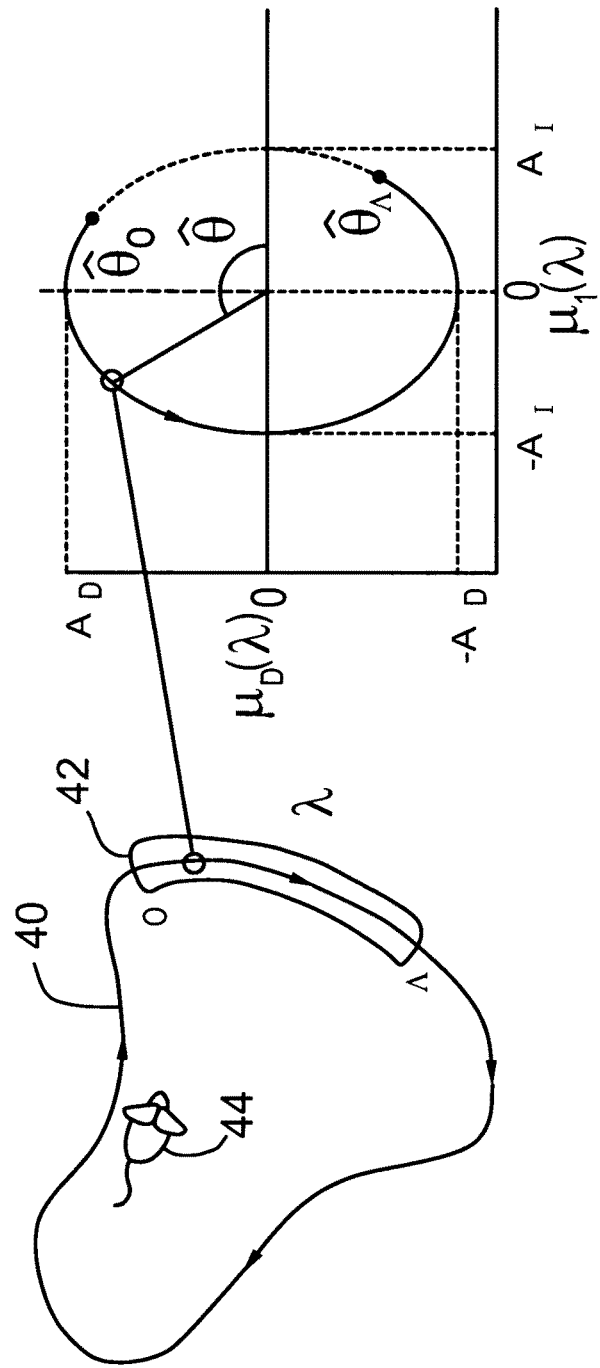
FIG. 6A shows an exemplary track and place field traversed in a clockwise direction that is mapped to a specific combination of integrating and differentiating mode contributions.

Theta phase precession and its specific attributes are modeled via a modification of the CRG network of FIG. 4A where precession reflects a shifting phase preference toward earlier phases. This differs from polarization-induced phase shifts in which phase preference does not change significantly. As is shown in FIG. 6A, the model assumes navigation of an animal 44 along a one-dimensional track 40, with a place field 42 belonging to the labile CRG outlined by a box. Mixing of modal outputs for the labile CRG depends on a distance metric $\lambda$, which is zero everywhere except inside the place field, where it monotonically increases on the interval 0 to $\Lambda$. As the animal 44 traverses the place field 42 in a clockwise direction, $\lambda$ is mapped to a two-dimensional ellipse that mathematically describes the co-variation of the integrating and differentiating mode contributions, thereby allowing for instantaneous phase of the gamma activity, relative to the population theta oscillation, to represent the location of the animal 44 in the place field 42. The modal coefficients of the labile CRG assume the following nonlinear form:

$$\mu_I(\lambda) = A_I \cdot \text{sgn}(\lambda) \cos\left(\left(\hat{\theta}_\Lambda - \hat{\theta}_o\right)\frac{\lambda}{\Lambda} + \hat{\theta}_o\right) \quad (16a)$$

$$\mu_D(\lambda) = A_D \cdot \text{sgn}(\lambda) \sin\left(\left(\hat{\theta}_\Lambda - \hat{\theta}_o\right)\frac{\lambda}{\Lambda} + \hat{\theta}_o\right). \quad (16b)$$

where $\hat{\theta}_o$ is the starting ellipse phase (as the animal 44 enters the place field 42), $\hat{\theta}_L$ is the stopping phase, $A_1$ and $A_D$ are the maximum magnitudes of the integration and differentiation mode contributions, respectively, and sgn(•) is the signum function. The signum function ensures that the labile CRG is off when the animal is outside the place field ($\lambda$=0).

The relationship of the theta phase $\theta$ to the phase of the ellipse $\hat{\theta}$ satisfies $\theta=2\pi-\hat{\theta}$; that is, as the elliptical phase advances forward (counter-clockwise direction), the theta phase precesses. $\Delta\theta=-(\hat{\theta}_L-\hat{\theta}_o)+\delta\theta$ is the extent of the total theta shift, where $\delta\theta$ is the uncertainty in the measurement due to added noise through the clock CRG, and the magnitude of $\Delta\theta$ is less than or equal to $2\pi$ radians.

The choice of elliptical mixing to characterize phase precession is convenient because of the unambiguous association of theta phase to modal amplitudes. The mixing need not be an explicit function of phase, as any variation will induce a phase shift relative to the theta oscillation. Straightforward elliptical encoding may be sufficient for simple applications (e.g. running along a one-dimensional track), but for cases in which the phase precession is highly nonlinear, or the phase relationship is more complex, then higher-order modes and nonlinearities may be required to define more elaborate n-dimensional closed-loop mixing geometries. Modal mixing is likely the result of network mechanisms, such as the dynamic interplay of excitation and inhibition, and if so, synaptic plasticity associated with exposure to a novel environment or rearrangement of a familiar environment would result in changes in the modal mapping, which in turn would translate into alteration of place field coding and phase precession.

Figure 6D:
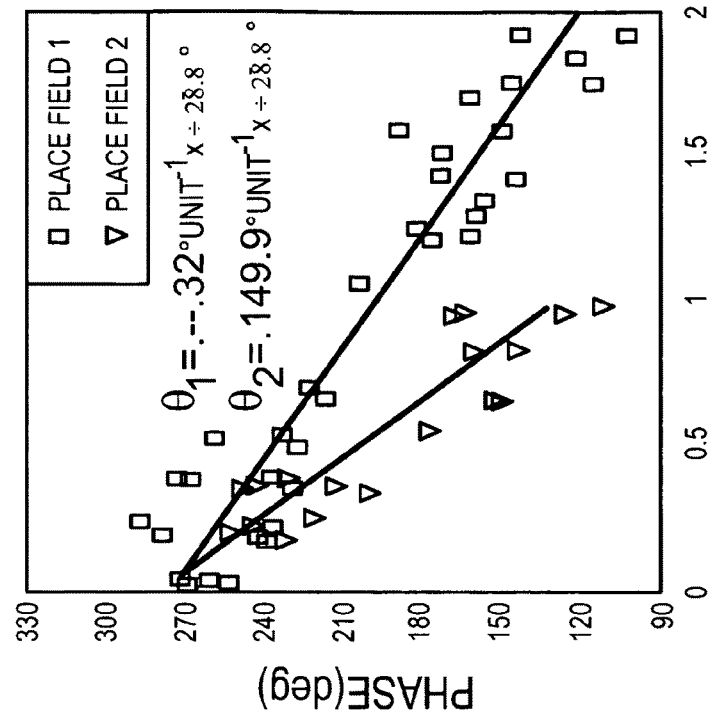
FIG. 6D shows a comparison of phase precession in two differently sized place fields.
Figure 6B:
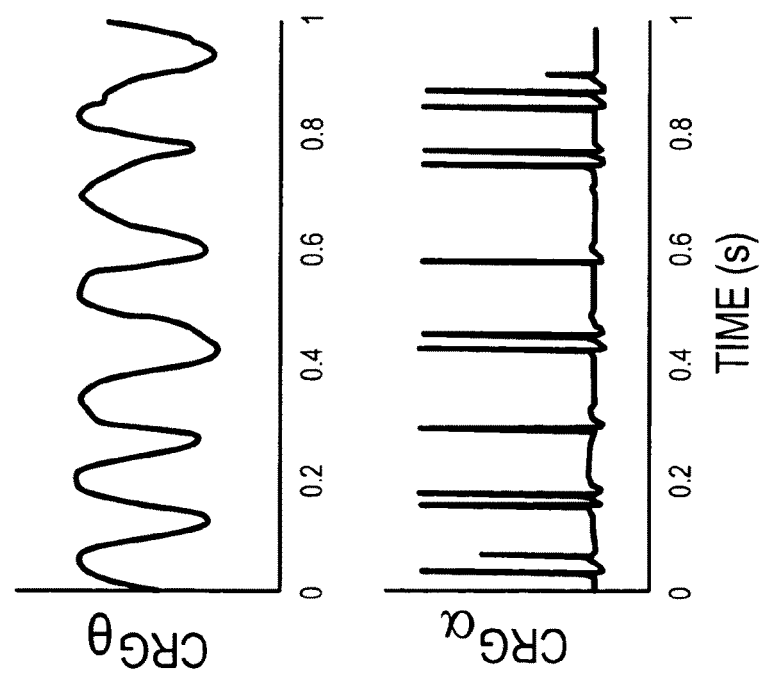
FIG. 6B shows phase precession induced by forward movement through the place field of FIG. 6A.
Figure 6C:
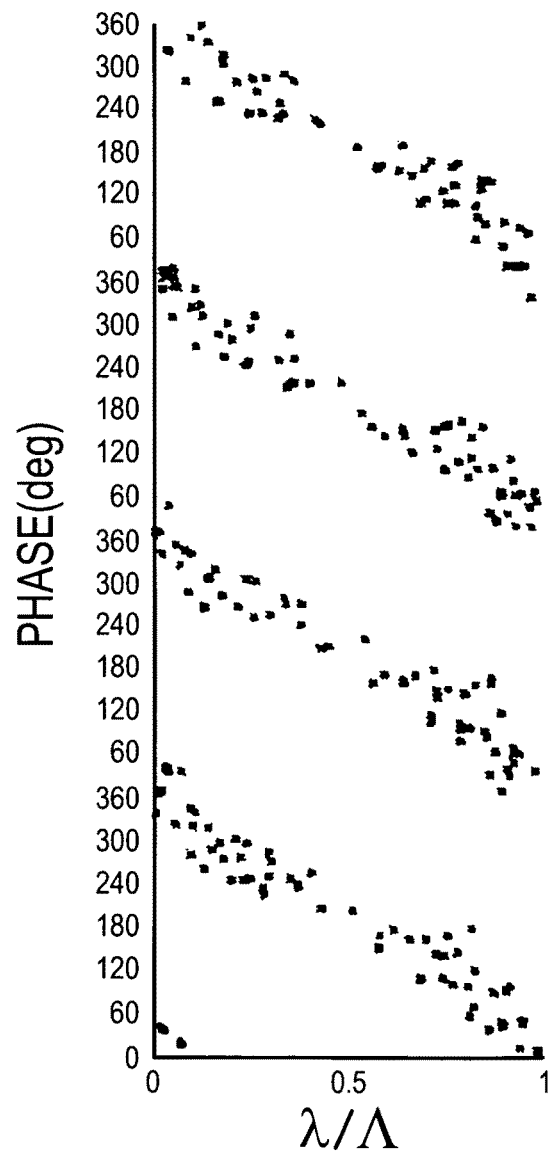
FIG. 6C shows a raster plot of gamma spikes as a function of theta phase over four consecutive traversals of the place field of FIG. 6A.

The time series of the clock and labile CRGs in FIG. 6B illustrate the phase relationship of the gamma activity as it precesses over one complete theta cycle ($\hat{\theta}_o=0$, $\hat{\theta}_L=2\pi$). The maximum modal amplitudes are set to $A_I=0.1$ and $A_D=0.5$. FIG. 6C shows a raster plot of the output of the labile CRG as a function of theta phase over four sequential traversals of the labile CRG's place field, with data collected from three runs. The phase completes an approximate shift of minus 360° over the place field length, and the relationship of phase to distance traversed is nonlinear, due to elliptical modal mixing (the descent slope is slightly steeper at the edges of the place field than near the center). For simplicity, only one place field is represented in the model, though there are no restrictions to extending the model, either by including several place fields for a single CRG, or by connecting more labile CRGs in parallel so that each fires within its own designated place field.

The effect of place field size $\Lambda$ on precession rate is presented in FIG. 6D, for phase parameters $\hat{\theta}_o=\pi/2$ and $\hat{\theta}_L=3\pi/2$. The parameters are changed to demonstrate a different phase mapping for precession (approximately 270° entry phase and 90° exit phase, for a total sweep of around −180°) instead of the complete cycle shown previously in FIGS. 6B and 6C. As can be seen in FIG. 6D, halving the place field size approximately doubles the precession rate, and the same result is obtained by doubling the running speed (d$\lambda$/dt) for constant place field size. Both results are consistent with experimental data of phase precession and place fields in navigating rats (O'Keefe and Burgess, Dual phase and rate coding in hippocampal place cells: theoretical significance and relationship to entorhinal grid cells, Hippocampus, 15:853-66, 2005). If the small place field average size of 28 cm is assumed, then the linearly-regressed model slope values (−77.32°/0.28 m=−276.1°/m, and −149.9°/0.28 m=−535.4°/m) are comparable in magnitude to experimentally measured slopes as shown in O'Keefe and Recce (Phase relationship between hippocampal place units and the EEG theta rhythm, Hippocampus, 3:317-30, 1993).

Phase precession in hippocampal CA3 and CA1 place cells appears to be controlled by upstream influences. The medial entorhinal cortex (MEC), which strongly innervates the hippocampal area CA3 and CA1, is purported to carry out path-integration that provides the animal awareness of direction and distance traveled (Hafting et al., Hippocampus-independent phase precession in entorhinal grid cells, Nature, 453:1248-52, 2008), but does not pinpoint its unique location in an environment. This differs from hippocampal place fields that are location-specific. The triangular tessellation of MEC grid cell activity (or firing rate) with space, correlated to the animal's movement, gives rise to a spatial code that is interpreted downstream of the MEC in the hippocampus. MEC spatial coding is the motivation for the coordinate metric in the CRG example of phase precession, as demonstrated in FIGS. 6A to 6D. The downstream translation of this code is mediated by nonlinear modal mixing, which results in shifting temporal phase preference of hippocampal place cell assemblies in relation to the theta rhythm. The superposition of upstream MEC grid cell fields with different spacings and orientations may constitute a form of spatial mode mixing, which could account for hippocampal place field activity—a possibility that is supported by experimental observations and mathematical models of MEC ensemble dynamics (Fyhn et al., Hippocampal remapping and grid realignment in entorhinal cortex, Nature, 446:190-4, 2007).

Example 4

System Identification and the Link to Neuronal Modes

Variation in response associated with nonlinear modal mixing enables changes in phase coding, as demonstrated in the case of theta precession. To quantify the input-output mapping differences between linear and nonlinear modal mixing, kernel estimation is performed using the Laguerre expansion technique (LET) on a single labile CRG with two different modal configurations, one linear, and the other, nonlinear. This is followed by extraction of the principal dynamic modes from the kernels, which allows for comparison to the neuronal modes of the model derived from Equation (2). For the linear case, modal mixing is defined by:

$$S_u = \epsilon_u(0.5\phi_I + 0.8\phi_D) \quad (17)$$

where the definition follows from Equation (3), and the channel gains are as listed in Table 1, except for setting $\epsilon_\gamma = \epsilon_\alpha$ to produce the observable output. For the nonlinear case, a quadratic nonlinearity is introduced, such that:

$$S_u = \epsilon_u(0.1\phi_I - 1.5\phi_D^2). \quad (18)$$

Figure 7A:
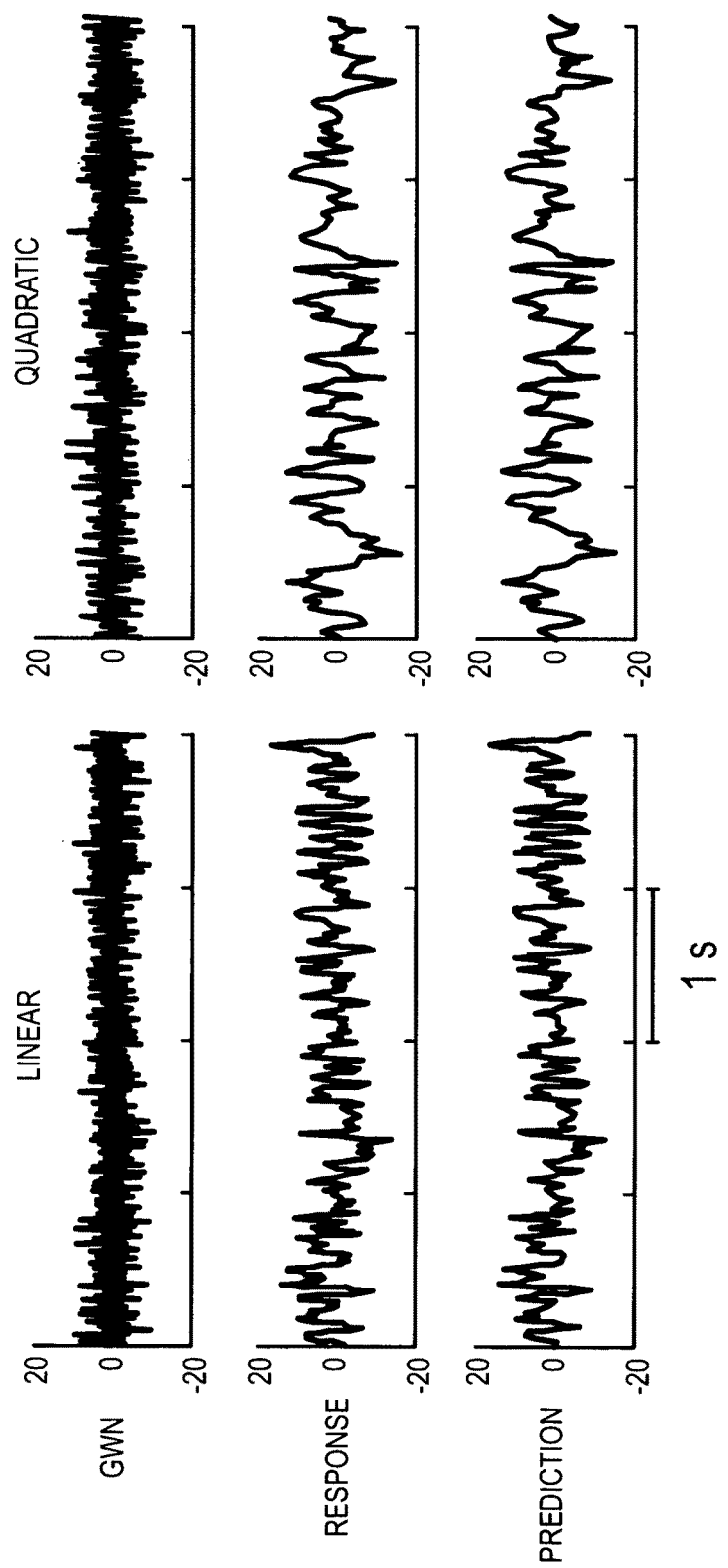
FIG. 7 shows an exemplary CGR model for linear and quadratic nonlinear modal mixing.
Figure 7B:
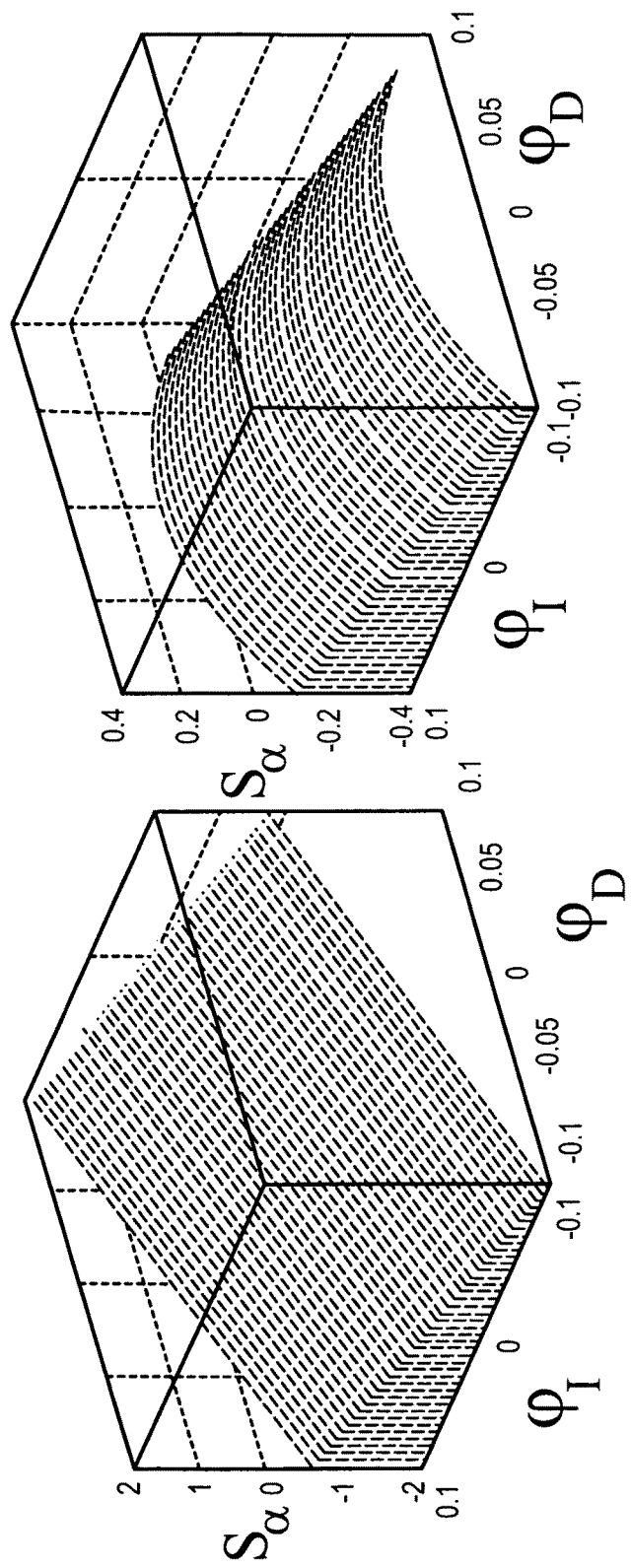

The quadratic form of nonlinearity is selected because it allows for a second-order kernel model to fully capture the input-output mapping of the CRG 10 (excluding the contribution of the ring device 14). FIG. 7 shows the response of the CRG using the alpha mixing channel as a reference, and the prediction of the kernel model. The left column is the linear case, and the right column, the quadratic nonlinear case. The surface plots at the bottom show the mixing plane geometry as a function of mode outputs. In this example, the percentage mean-squared error, Equation (12), is 0.0026% and 0.0032% for the linear and quadratic cases respectively where Equation 12 is computed for the least-squares regression of the Laguerre expansion coefficients to fit the response, Equation (8), and determine the kernels, Equations (11a) to (11c). For the prediction, the error is 0.0029% and 0.0038%, respectively.

Figure 8A:
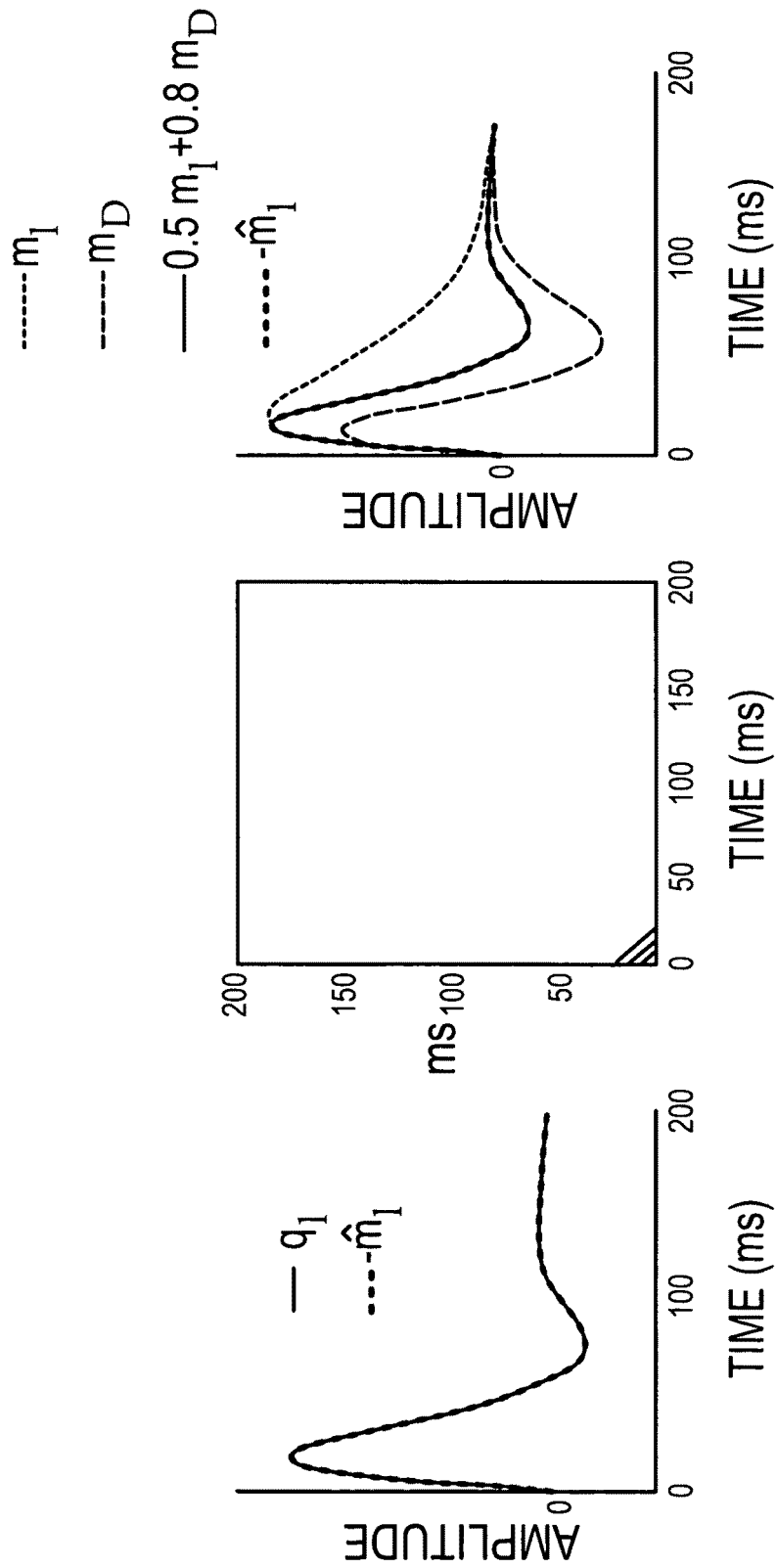
FIG. 8A shows an exemplary linear model of model response characteristics.
Figure 8B:
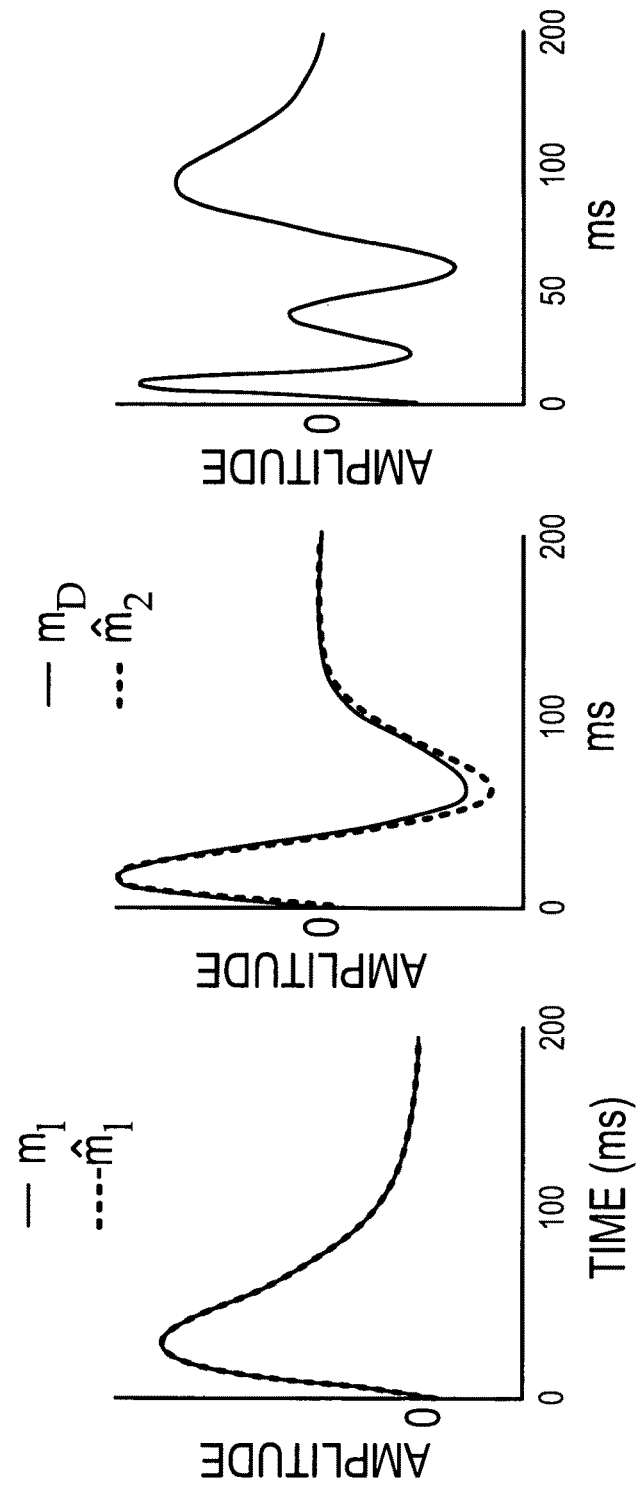
FIG. 8B shows an exemplary quadratic model of model response characteristics.
Figure 8C:
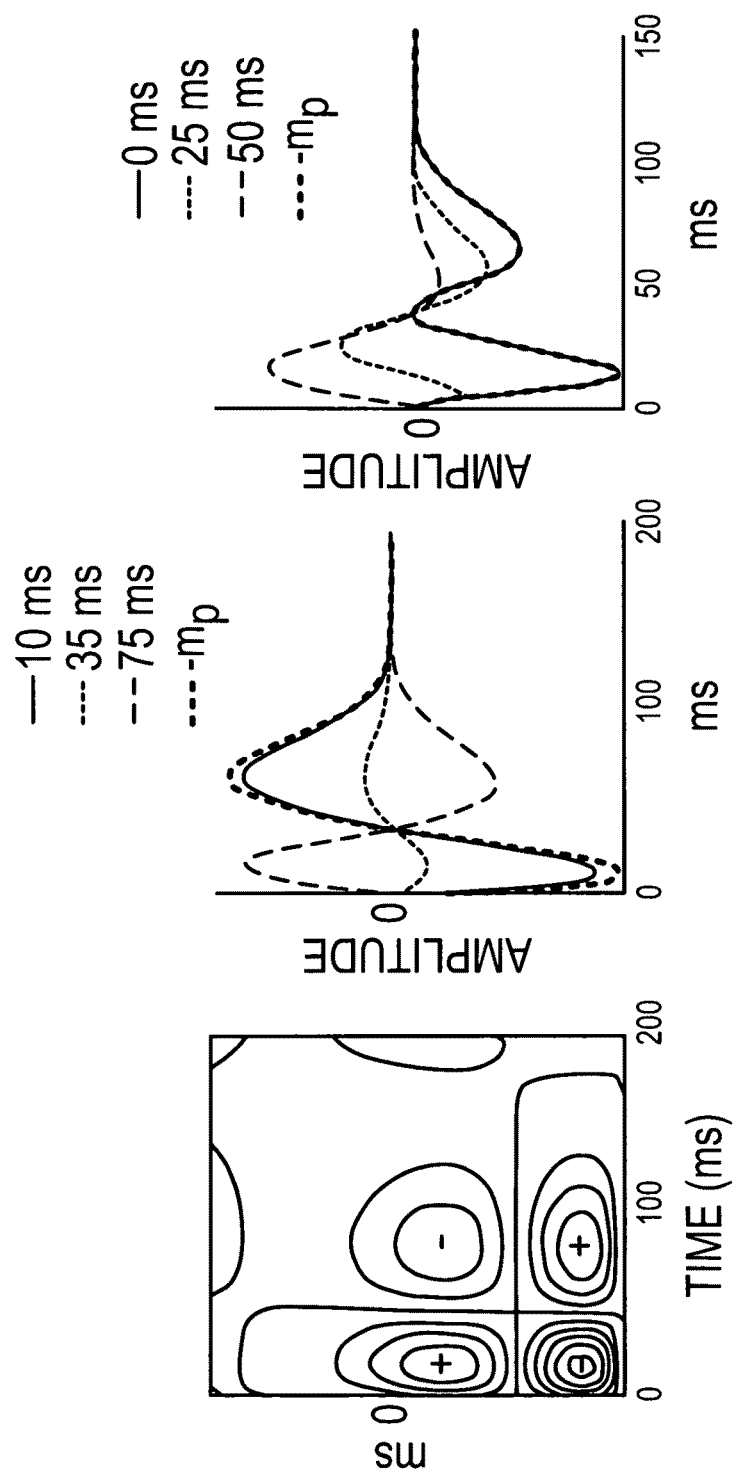
FIG. 8C shows an exemplary quadratic second-order kernel properties of model response characteristics.

Principal dynamic modes (PDMs) are extracted from the kernels by eigen-decomposition and selected on the basis of their corresponding eigenvalues at the 0.5% significance level, as defined by Equation (15). In the linear example, only one PDM is obtained and its inverted amplitude profile (its eigenvalue was negative) is found to correspond directly to the first-order kernel and the linear weighting of the integrating and differentiating modes specified by Equation (17) as shown in FIG. 8A. The second-order contribution is negligible, since the response could be completely characterized by the first-order kernel, which matched the form of the PDM. For the quadratic case, three PDMs are isolated at the 0.5% significance level FIG. 8B. The first PDM corresponds to the integrating mode as well as the first-order kernel, and the last two PDMs correspond to the second-order kernel (and differentiating mode). The second order kernel has two peaks and two troughs, shown in the left diagram of FIG. 8C, and the kernel cross-sections parallel to the axis reflect the biphasic form of the differentiating mode as seen in the center diagram of FIG. 8C, while the cross-sections parallel to the diagonal reflect the quadratic transformation of the differentiating mode, as seen in the right diagram of FIG. 8C.

The cross-sections of the second-order kernel reveal how input-dependent variation in the model response is achieved by having a quadratic nonlinearity. The second-order kernel maps the nonlinear response of the system to a pair of impulses at different time lags. Depending on when the impulses occur relative to one another, a different response is generated. For time interval T between the pulses, the amplitude profile of the second-order system response corresponds to the T-diagonal cross-section of the kernel. The second-order kernel is symmetric so it does not matter which pulse is lead and which is lag. When the individual impulses are spaced at intervals greater than the memory of the kernel, the quadratic response corresponds to the zero-diagonal of the second-order kernel. As the spacing between the impulse pair narrows (i.e. the instantaneous frequency goes up), the profile changes in a manner consistent with the kernel's cross-section at the given time lag. Hence the nonlinear model is able to decode both temporal information and frequency information. The response becomes more complicated for inputs other than impulses, such as spike trains or multiphasic inputs. The contribution of the first-order mode is not affected by pulse intervals, which explains why linear mixing does not produce input phase or frequency-dependent variations.

Figure 9A:
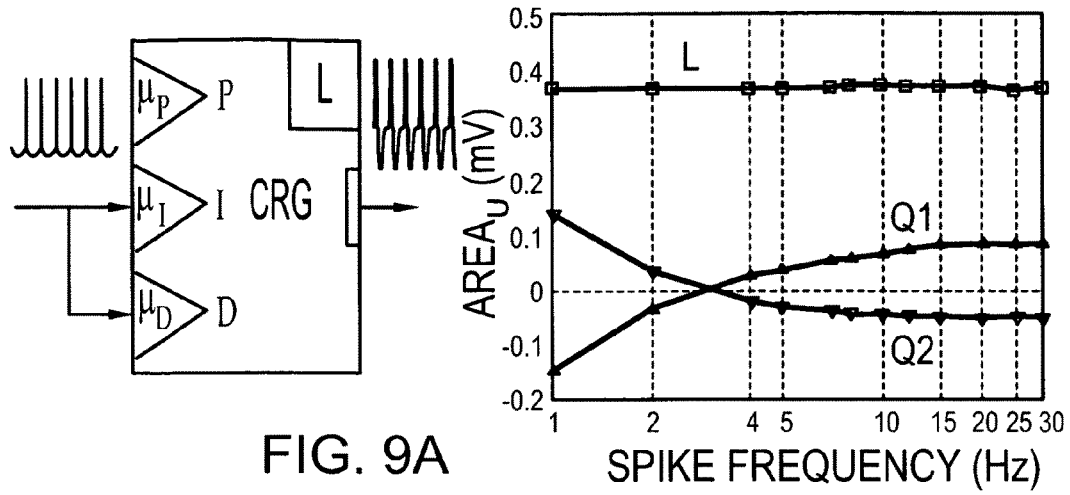
FIG. 9A shows an exemplary labile CRG frequency response to input spike trains over a range of frequencies with respect to the linear model, the quadratic mode, and a second quadratic model.
Figure 9B:
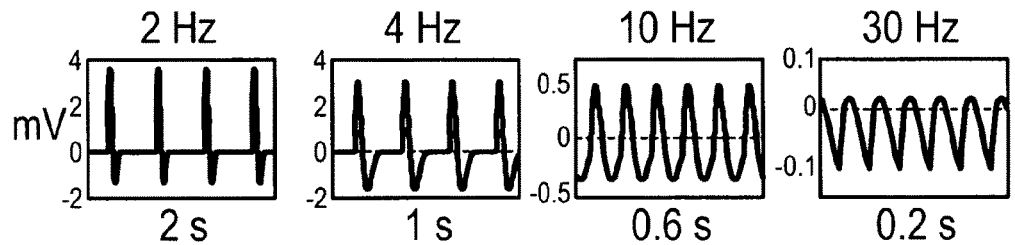
FIG. 9B shows an exemplary subthreshold output of the second quadratic model of FIG. 9A at various input frequencies.
Figure 10:
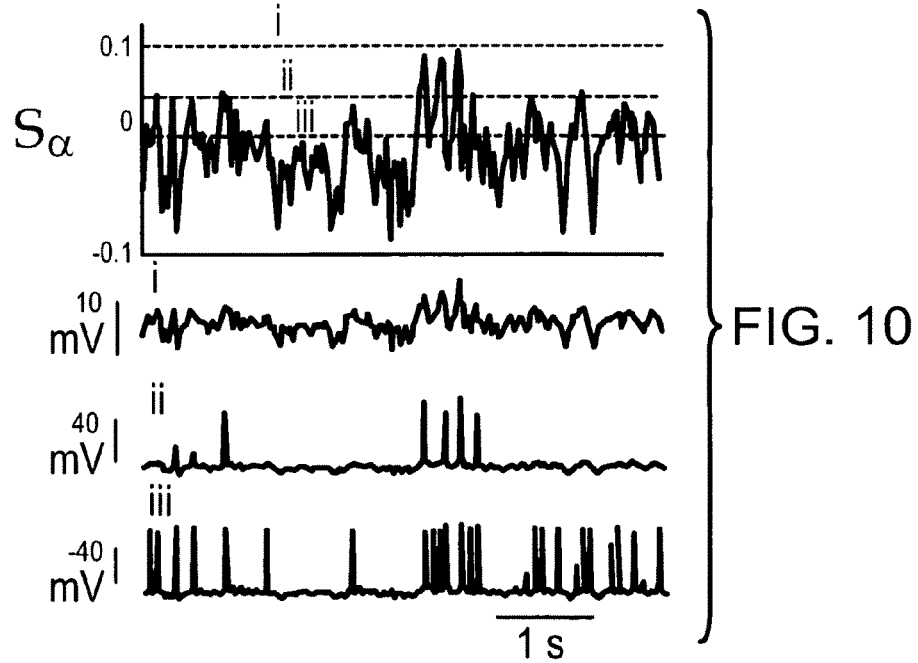
FIG. 10 shows exemplary coding of output phase and rate for quadratic modal mixing.

FIGS. 9A and 9B analyze the subthreshold response of linear and quadratic CRGs to input spike trains delivered at frequencies from 1 to 30 Hz. The activation threshold in Equation (5b) is raised sufficiently to prevent activation of the ring device and prevent any spikes at the output. The response is quantified by measuring the area under the curve per unit time (in millivolt-seconds per second), using the trapezoidal method of integration, as shown in FIG. 7A. The linear model is not dependent on the input frequency, whereas the quadratic model displays a distinct frequency-dependent switching from inhibition to excitation, or vice versa, depending on which mode contribution is squared. The mixed modal output also varies its shape and polarity in a manner consistent with the changing frequency, as seen in FIG. 9B. This switching phenomena has been described in hippocampal networks with disynaptic feedforward inhibition (Klyachko and Stevens, Excitatory and feed-forward inhibitory hippocampal synapses work synergistically as an adaptive filter of natural spike trains, PLoS Biol, 4:e207, 2006). FIG. 10 demonstrates the output of quadratic model as defined by Equation (18) for different activation thresholds as set in Equation (5b). The ring device 14 translates suprathreshold modal responses into output spikes, coding for phase (spike placement) and rate (spike frequency).

Example 5

Rate-Coding and Disynaptic Feedforward Inhibition

If the CRG model of neural coding operates on the premise that the bank of neuronal modes 12 is representative of the effect of cellular and network mechanisms, then an expanded model using fewer modes and simpler modal mixing—but with a more complex network topology or parameterization—should be able to generate results that are comparable to the compact model. In this regard, the frequency-dependent switching of a quadratic CRG is reproduced with networks constructed to resemble the disynaptic inhibitory circuits described in literature, using only CRGs with proportional and integrating modes (but no differentiating modes) and linear modal mixing in order to simulate synaptic connections.

Figure 11A:
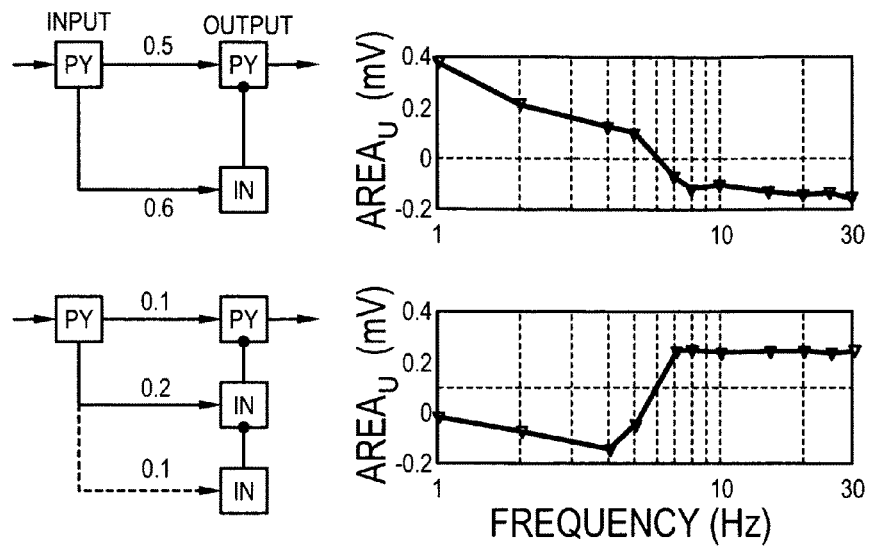
FIG. 11A is a schematic diagram for an excitatory-to-inhibitory transition network configuration and its corresponding frequency response.
Figure 11B:
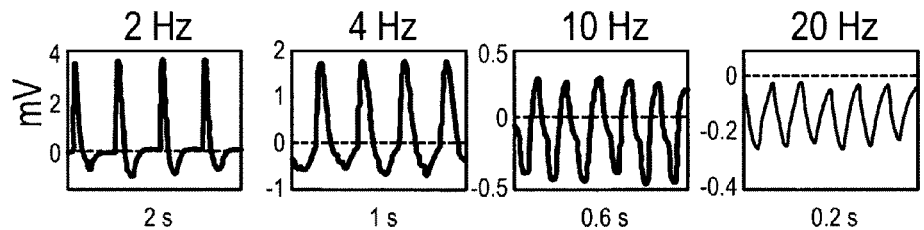
FIG. 11B is a schematic diagram for an inhibitory-to-excitatory transition network configuration and its corresponding frequency response.
Figure 11C:
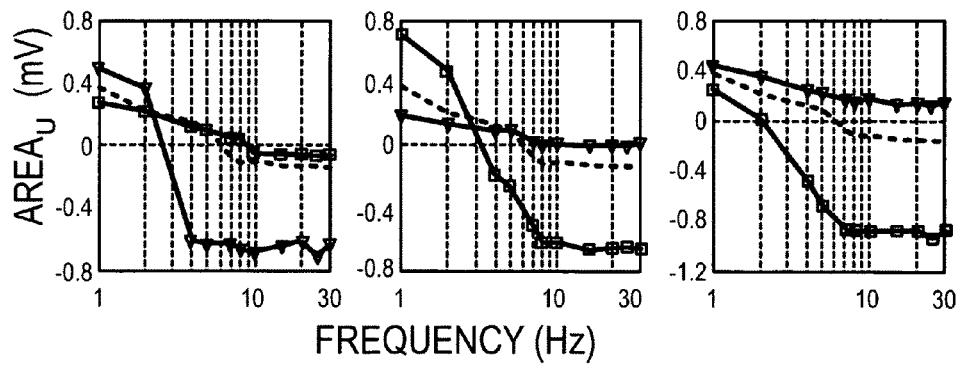
FIG. 11C shows the subthreshold output response waveforms of the circuit of FIG. 11A.

FIG. 11A shows two network configurations and their corresponding frequency responses. PY units represent excitatory pyramidal neurons, and IN units represent inhibitory interneurons. The input PY was stimulated to produce a spike train at the desired frequency, and the subthreshold response of the circuit was recorded at the output PY and integrated to find the area under the curve per unit time. The first network (top) has a single disynaptic inhibitory connection, and codes an excitatory-to-inhibitory transition with increasing firing frequency of the input pyramidal unit. The second network (bottom) has an additional disynaptic inhibitory connection that inhibits the first network, and the entire circuit codes an inhibitory-to-excitatory transition. The frequency-dependent variation associated with modal mixing, seen in FIG. 11B, is similar in form to that described in the quadratic CRG of FIG. 9B. Even though the mixing is linear in the network model, the nonlinearities associated with network coupling enable frequency switching to occur. Changing model parameters such as the modal decay constant (from Equation (2)) and network connection strengths affects the slope and zero-crossing of the frequency response as shown in FIG. 11C, highlighting that synaptic plasticity plays an integral role the development of coding relationships (Lever et al., Nature, 416:90-4, 2002).

Figure 12:
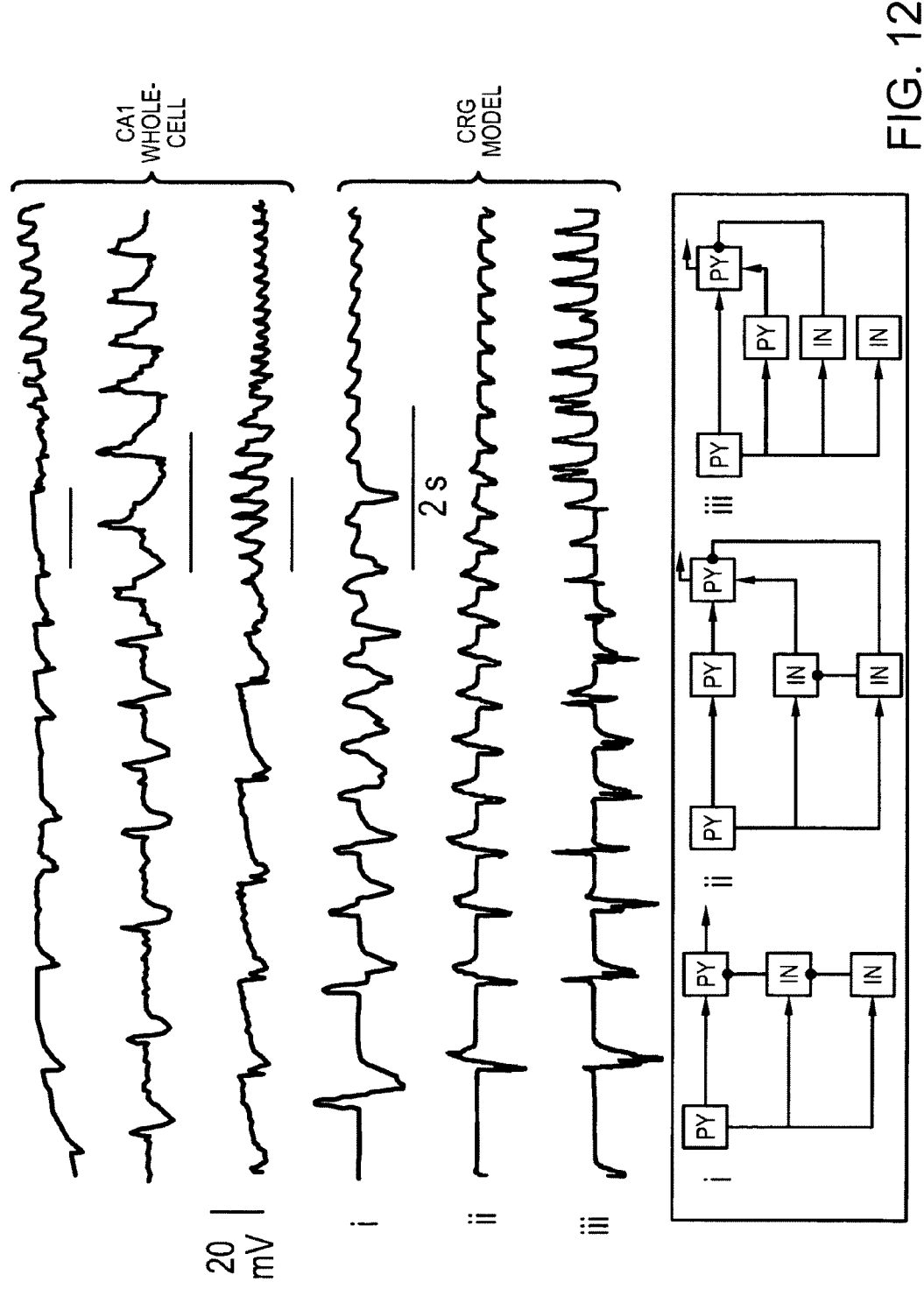
FIG. 12 shows exemplary frequency-associated transitions in the hippocampus.

FIG. 12 provides a visual comparison of subthreshold responses of CRG disynaptic inhibitory networks with whole-cell recordings of hippocampal CA1 pyramidal neurons prepared under low magnesium conditions (see Derchansky et al., Model of frequent, recurrent, and spontaneous seizures in the intact mouse hippocampus, Hippocampus, 14:935-47, 2004 and Tancredi et al., Brain Res, 511:280-90, 1990) exhibiting frequency-associated transitions in activity. The results of the model suggest feedforward inhibitory networks may serve to process upstream temporal or rate codes due to their frequency selectivity and switching properties.

Nonlinear modal mixing is indicative of a network mechanism, as was demonstrated by substituting the quadratic CRG in FIG. 9A with a network model that generated a very similar input-output mapping as in FIG. 11A. Disynaptic feedforward inhibition coupled with synaptic excitation is one possible mechanism for reading out the MEC code because the combination has been shown to facilitate nonlinear frequency-dependent transitions in the level of excitation to inhibition and in the phasic profile of responses (Mori et al., A frequency-dependent switch from inhibition to excitation in a hippocampal unitary circuit, 431:453-6, 2004). Circuits that map changes in frequency to changes in output response are plausible agents for deciphering rate codes. The major hippocampal pathways, such as the mossy fiber pathway (DG→CA3), Schaeffer collaterals (CA3→CA1), and perforant path (EC→CA3/CA1), contain disynaptic feedforward inhibitory connections that confer adaptive frequency characteristics (Empson and Heinemann, The perforant path projection to hippocampal area CA1 in the rat hippocampal-entorhinal cortex combined slice, J Physiol, 484(Pt 3):707-20, 1995). Disynaptic inhibition is also widely distributed across other segments of the central nervous system, including thalamocortical circuits (Inoue and Imoto, Feedforward inhibitory connections from multiple thalamic cells to multiple regular-spiking cells in layer 4 of the somatosensory cortex, J Neurophysiol, 96:1746-54, 2006), which regulate the flow of sensory information through the thalamus to the neocortex, projections of the superior colliculus in the oculomotor system (Yoshida et al., Disynaptic inhibition of omnipause neurons following electrical stimulation of the superior colliculus in alert cats, J Neurophysiol, 85:2639-42, 2001), responsible for eye saccades, vestibular system afferents, which relay signals related to head movements (Uchino et al., Excitatory and inhibitory inputs from saccular afferents to single vestibular neurons in the cat, J Neurophysiol, 78:2186-92, 1997), cortical microcircuits (Silberberg and Markram, Disynaptic inhibition between neocortical pyramidal cells mediated by Martinotti cells, Neuron, 53:735-46, 2007), and corticospinal fibers affecting spinal tract motor neurons (Parker, Activity-dependent feedforward inhibition modulates synaptic transmission in a spinal locomotor network, J Neurosci, 23:11085-93, 2003), amongst others. These circuits are strategically positioned to gate the transfer of information between neuronal populations, and it is hypothesized that they process upstream temporal or rate codes, owing to their frequency-selective properties, and may therefore be able to control or facilitate downstream forms of coding, such as hippocampal phase precession.

Example 6

Adaptation of the CRG to a Biological System

Generally, the CRG 10 provides a practical methodology for cloning input-output dynamics of any biological system. The procedure involves fitting the coefficients of a generalized power series of order N, consisting of K principal dynamic modes (derived from established methods described above), to the recorded output of the biological system in response to J inputs of the CRG 10:

$$S_y(t) = \mu_0 + \sum_{n=1}^{N} \sum_{k=1}^{K} \sum_{j=1}^{J} \mu_{n,k,j} (\hat{m}_k(t) * x_j(t))^n \quad (19)$$

where $S_y(\bullet)$ is the fitted static nonlinearity implemented in the CRG; $\mu_{n,k,j}$ is the nth-order coefficient of the kth modal output pertaining to the jth input; $x_j(t)$ is the jth input, $\hat{m}_k(t)$ is the kth PDM. The asterisk denotes the convolution operation that yields the kth modal output:

$$\hat{m}_k(t) * x_j(t) = \int_0^\infty \hat{m}_k(\tau) x_j(t-\tau) d\tau. \quad (20a)$$

$$\approx T_s \sum_{\tau=1}^{M} \hat{m}_k(\tau) x_j(t-\tau) \quad (20b)$$

where Equation (20b) is the discrete convolution approximation to Equation (20a), M is the length in samples (memory) of the truncated PDMs, and $T_s$ is the sampling period. A suitable regression or optimization method for finding the parameters of Equation (19) is needed, such as least-squares or minimax. For a least-squares fitting, the optimization problem can be phrased in the manner:

$$\text{Find argmin}_{\mu} \left\{ \sum_{t=T_s}^{RT_s} [S_y(t; \mu_0; \{\mu_{n,k,j}\}) - y(t)]^2 \right\} \forall \, n, k, j \quad (21)$$

where y(t) is the recorded output of the biological system, and R is the record length in samples. Equation (19) serves as the basic form of the static nonlinearity of the CRG 10. If the biological system has multiple extrinsic or intrinsic outputs (intrinsic outputs being internal to the system, such as in the case of intra-network coupling), then an equivalent number of fitted nonlinearities are required, one for each CRG 10 representing an output in the multi-output context. Therefore, the total number of parameters to be fitted depends on CRG network size and the order of the nonlinearities.

The generalized modal power series, Equation (19), provides a coding formalism that is mathematically related to the Volterra series, but instead of presenting with difficult higher-order convolutions involving n-dimensional kernels, the modal series simplifies the model description to K×J first-order convolutions involving one-dimensional modes and scalar coefficients. Unlike many types of functional expansions that require orthogonality of the basis functions, the modal power series does not require strict independence of the modes for the model to be valid; this follows from the non-orthogonality of the Volterra kernels from which the modes are derived.

Figure 13A:
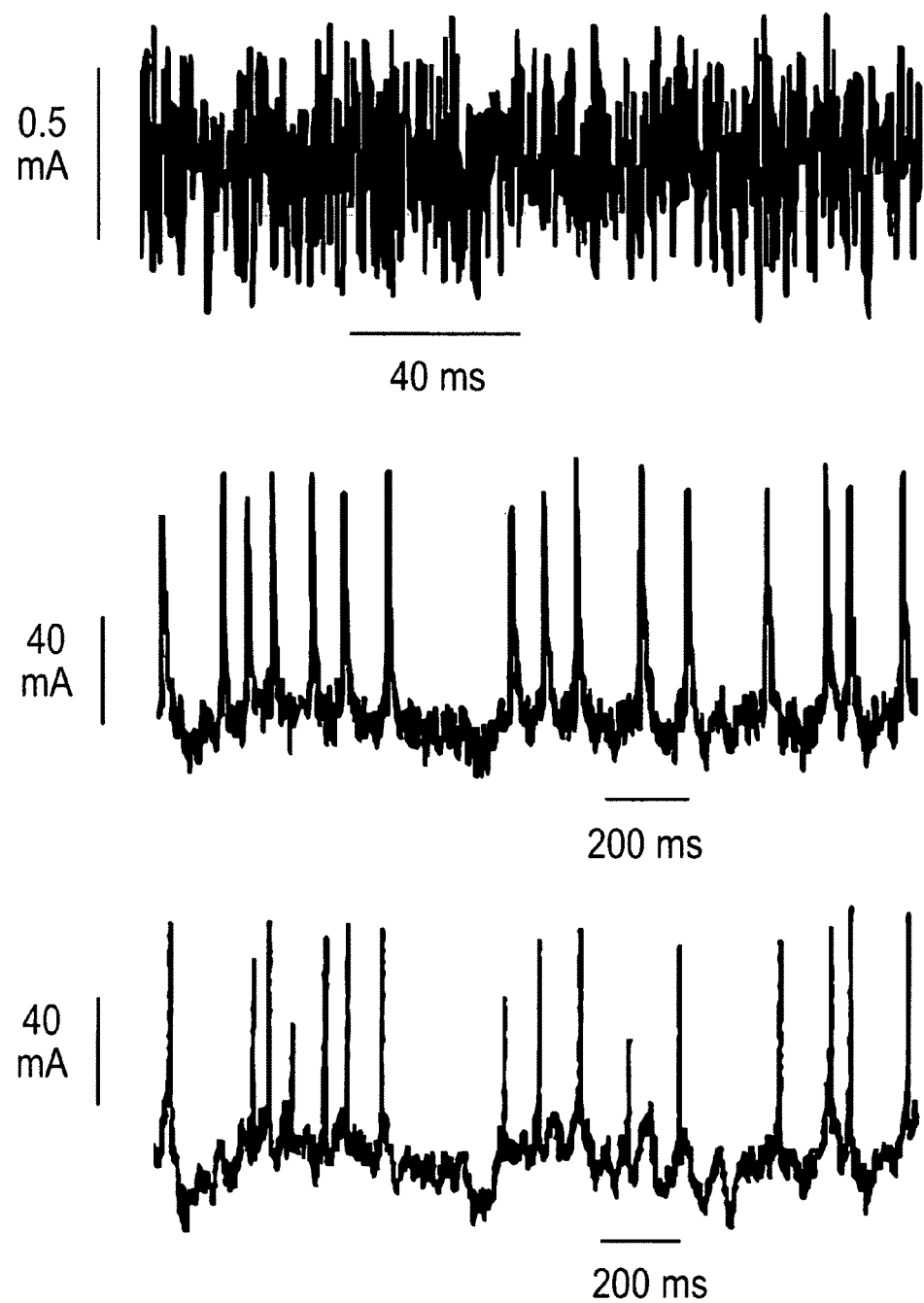
FIG. 13A shows an exemplary labile CRG representation of a spiking neuron.
Figure 13B:
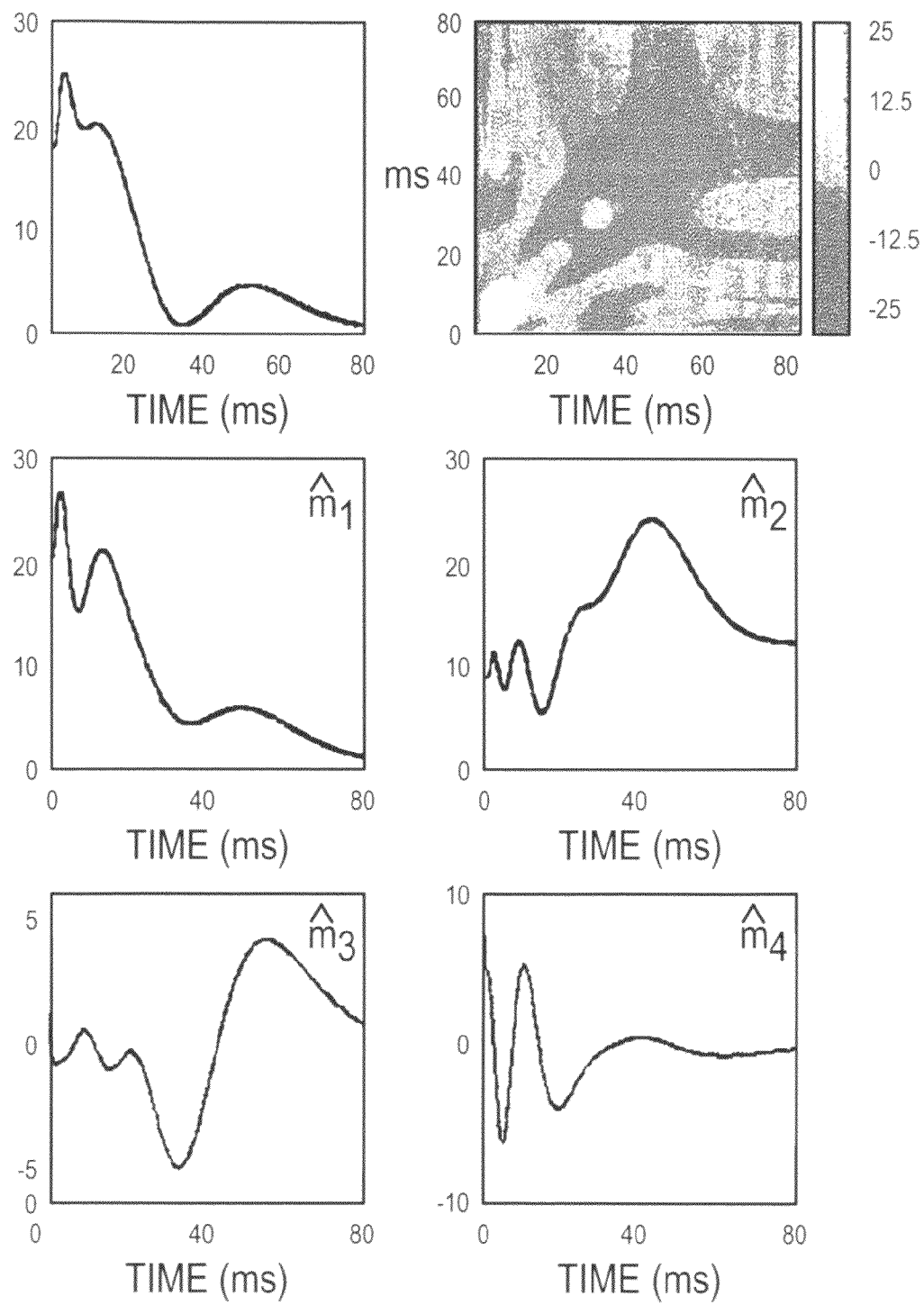
FIG. 13B shows the first and second order kernels of the recorded exemplary neuron of FIG. 13A, and the 4 principal modes derived from the first and second order kernels that were used in the exemplary labile CRG representation in FIG. 13A.

An exemplary adaptation of the CRG 10 to a real biological system is illustrated in FIGS. 13A and 13B. In the top trace of FIG. 13A, a sample trace of Gaussian white noise (GWN) current stimulus delivered to patch-clamped CA3 pyramidal cell in a hippocampal slice preparation is shown. The total duration of the stimulus of 1.8 seconds. In the middle trace of FIG. 13A, a response of CA3 neuron to the 1.8 second GWN stimulus is shown. In the bottom trace of FIG. 13A, the response of a labile CRG to an identical GWN stimulus is shown. The parameters of the CRG are configured to model the dynamic response of the recorded pyramidal neuron. The top diagram of FIG. 13B shows first- and second-order kernels, respectively, of the recorded neuron from FIG. 13A. The principal dynamic modes, or PDMs, (1-4) derived from kernels at the 5% significance level are shown below in FIG. 13B. The PDMs are inserted into the labile CRG mode bank and fitted to the biological system. The units of amplitude in this example are: for the first-kernel and PDMs, mV/(nA·ms); and for the second-order kernel, mV/(nA·ms)$^2$.

In this example, a pyramidal neuron is sampled from within the CA3 network of the hippocampus, using a whole-cell patch electrode for stimulation and recording. Details of the methodology are provided in Kang et al., (Transformation of neuronal modes associated with low-Mg2+/high-K+ conditions in an in vitro model of epilepsy, J Biol Phys, In Press, 2009), the contents of which are herein incorporated by reference. The response of the biological system, as elicited by the GWN current injection x(t) is used to construct a second-order kernel model via LET, and the subsequently identified principal dynamic modes were incorporated into the CRG model via a second-order fitted nonlinearity of the form:

$$S_y(t) = \mu_0 + \sum_{k=1}^{4} \mu_{k,1}(\hat{m}_k(t) * x(t)) + \sum_{k=1}^{4} \mu_{k,2}(\hat{m}_k(t) * x(t))^2 \quad (22a)$$

$$S_\alpha(t) = \varepsilon_{py} S_y(t) \quad (22b)$$

$$S_\phi(t) = 10^2 S_\alpha(t) \quad (22c)$$

where Equations (22b) and (22c) are the normalized and scaled versions of Equation (22a), used to feed the labile ring device encoding the output spikes. The coefficients of Equation (22a), $\mu_{k,j}$, are estimated by least-squares fitting of the modal response to the biologically-recorded response: $\mu_0=4.1381$ mV, $\mu_{1,1}=5.1989$, $\mu_{2,1}=-0.6112$, $\mu_{3,1}=-0.0350$, $\mu_{4,1}=0.0024$, $\mu_{1,2}=0.1744$/mV, $\mu_{2,2}=-0.4695$/mV, $\mu_{3,2}=-0.1612$/mV, $\mu_{4,2}=-0.0808$/mV. The static nonlinearities feeding the ring device 14 in this example are normalized by the factor $\varepsilon_{PY}=1/\max\{|S_y|\}=0.0376$/mV. Satisfactory coding of output spike phase is achieved with labile ring parameters $\omega=\pi$rad/s (0.5 Hz), and excitation threshold 0.2.

The hippocampal neuron in FIGS. 13A and 13B does not exhibit any discernable rhythmicity in either its baseline or spiking response. In cases where distinct rhythms are present and need to be included in the model representation, parameters such as intrinsic frequencies, refractory periods, and waveform shape may be quantified from time-frequency decomposition of the biological time series, using specialized techniques to isolate the individual rhythms as described in Zalay et al., (A wavelet packet-based algorithm for the extraction of neural rhythms, Ann Biomed Eng, 37:595-613, 2009), the contents of which are herein incorporated by reference.

Example 7

Simulation of a CRG Hippocampal Network

Figure 14C:
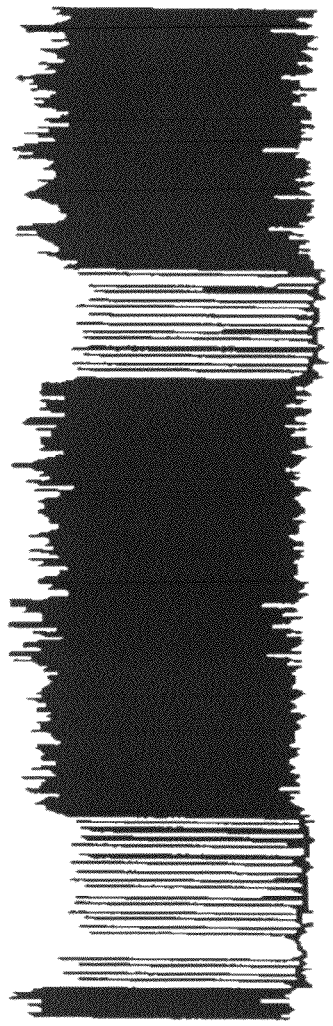
Figure 14D:
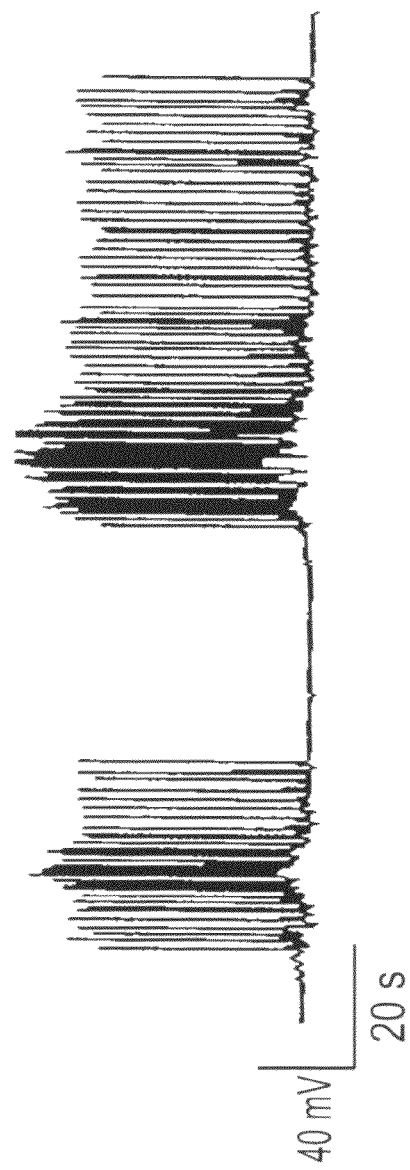

FIGS. 14A to 14D provide an example of a network containing four (4) CRGs. This hippocampal CRG network model is parameterized to generate spontaneous seizure-like activity and was simulated on a computer system. Pyramidal assemblies $P_1$ and $P_2$ were reciprocally coupled via excitatory synapses. Interneuronal assemblies $I_1$ and $I_2$ provided the pyramidal units $P_1$ and $P_2$ with feedback inhibition. For comparison, traces experimentally recorded from a hippocampal slice preparation undergoing seizure-like activity are presented alongside the simulated results from the CRG network in FIGS. 14E and 14F. In FIG. 14A, the voltage activity of pyramidal unit $P_1$ was simulated under non-seizing conditions. FIG. 14B shows that decreasing the integrating mode decay rate increased network excitability and induced spontaneous seizure-like events. In the inset of FIG. 14B, the transition into and out of tonic seizing was marked by a shift in spike frequency and bursting magnitude. FIG. 14C shows that strengthening the network coupling connections increased the severity of ictal activity. FIG. 14D shows that the intermittency of seizure-like activity was controlled by changing DC bias of the units in the network relative to one another.

Example 8

Effective Control of Seizure-Like Events

Figures 15A, 15B:
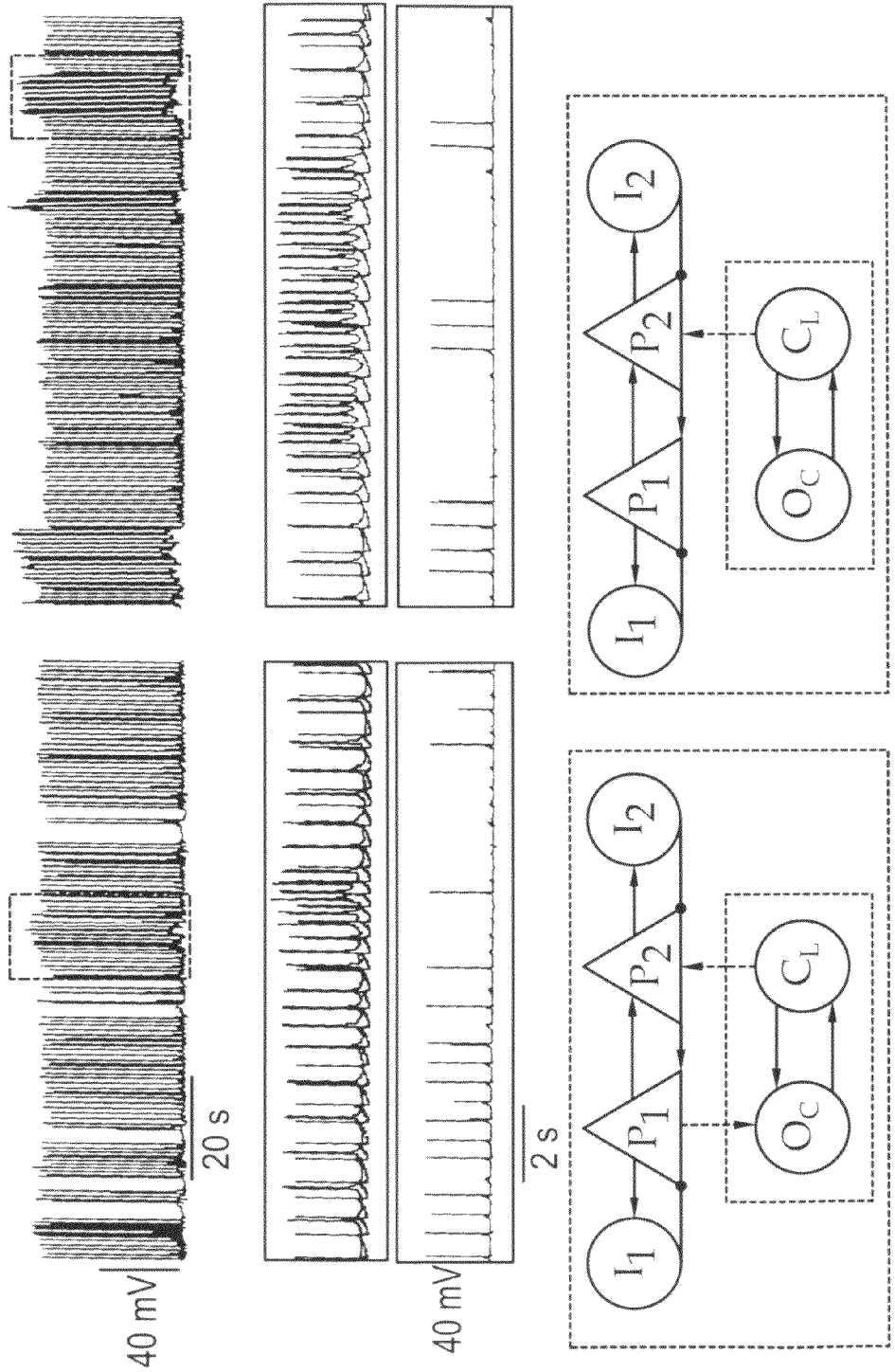
FIG. 15A shows a therapeutic CRG network containing two bidirectionally coupled CRG therapeutic units.
FIG. 15B shows a therapeutic CRG network containing two coupled CRG therapeutic units with a broken control loop.

Using the same simulated hippocampal network of Example 7 under epileptiform conditions, a therapeutic CRG network, containing two bidirectionally coupled therapeutic CRGs, was interfaced to the seizing network with both a simulation pathway and a recording pathway, forming a closed control loop as shown in FIG. 15A. The therapeutic CRG network parameters and coupling strengths were tuned until adequate control was achieved, without being disruptive to network activity. The seizing network was sampled by $O_C$, the observer unit (a clock CRG), and the dynamic simulation was delivered by $C_L$, the controller unit (a labile CRG). The boxed portion of the top trace examines a region where a probable seizure-like event was about to occur and the two middle traces examine the response of $O_C$ (top box) and $C_L$ (bottom box), respectively, where the response of $O_C$ (red) was seen to track that of $P_2$, just as the activity of $P_2$ began its seizure-like event transition. The transition was stopped and intermittency was re-established.

FIG. 15B used the same simulation conditions as FIG. 15A, however, the control loop was broken by removing the observer input to $O_C$, thereby eliminating the feedback that adjusts the dynamic response of the therapeutic CRG network. As a result, the activity of $O_C$ failed to track the seizure-like event transition and a full seizure-like event occurred, in spite of stimulation still being delivered through $C_L$.

Although embodiments have been described above with reference to the drawings, those of skill in the art will appreciate that variations and modifications may be made without departing from the spirit and scope thereof as defined by the appended claims.

What is claimed is:

1. A method of electrically stimulating a nonlinear biological system, the method comprising:
   transforming an input signal using a plurality of dynamic modes to generate a plurality of modal outputs, the dynamic modes being configured to provide a functional representation of the input and output properties of said nonlinear biological system, and each dynamic mode performing a unique transformation of the input signal;
   scaling and combining the modal outputs using a plurality of mixing functions;
   applying the scaled and combined modal outputs to a ring device in the form of an oscillator that generates rhythm output represented by amplitude and phase variables, said modal outputs modifying the dynamics of said ring device in a time-dependent manner to modify the rates of change of the amplitude and phase variables;
   mapping the amplitude and phase variables to an external observable variable to generate a physiologically-representative and observable output electrical stimulation signal; and
   stimulating said nonlinear biological system with said physiologically-representative and observable output electrical stimulation signal via an electromechanical interface.

2. The method of claim 1 wherein the scaled and combined modal outputs that are applied to the ring device are applied to a clock that generates a continuous rhythmic output and a labile clock that generates a non-continuous rhythmic output, said scaled and combined modal outputs modifying the amplitude and frequency of the continuous rhythmic output of the clock and the amplitude and frequency of the non-continuous rhythmic output of the labile clock, the amplitudes and frequencies of the rhythmic output and the non-continuous rhythmic output forming the rhythm output generated by the ring device.

3. The method of claim 1 wherein said dynamic modes are neuronal modes selected from the group consisting of zero-order neuronal modes, first-order neuronal modes, second-order neuronal modes, third-order neuronal modes, and combinations thereof.

4. The method of claim 3 wherein each of the plurality of neuronal modes transforms a respective component of the input signal to generate a corresponding modal output.

5. The method of claim 3 wherein the unique transformation of the input signal is based on shape, decay rate and length of the dynamic mode.

6. The method of claim 5 wherein the dynamic modes are extracted from Eigen-decomposition of measured kernels that encode the dynamic response of the nonlinear biological system.

7. The method of claim 6 wherein the kernels are Volterra or Wiener kernels that encode the dynamic response of the nonlinear biological system through a respective Volterra or Wiener functional series.

8. The method of claim 1 wherein the biological system comprises a neuron.

9. The method of claim 1 wherein the biological system is a brain region.

10. The method of claim 9 wherein said brain region is stimulated to prevent, control or treat seizures.

11. The method of claim 1 wherein each dynamic mode acts as an integrator, a differentiator or a combination thereof.

12. A method of electrically stimulating a nonlinear biological system, the method comprising:
    transforming an input signal using a plurality of dynamic modes to generate a plurality of modal outputs, the dynamic modes being configured to provide a functional representation of the input and output properties of said nonlinear biological system, wherein each dynamic mode uniquely transforms the input signal, wherein the unique transformation of the input signal is based on shape, decay rate and length of the dynamic mode and wherein the dynamic modes are extracted from Eigen-decomposition of measured kernels that encode the dynamic response of the nonlinear biological system;
    applying said modal outputs to a ring device in the form of an oscillator that generates rhythm output represented by amplitude and phase variables, said modal outputs modifying the dynamics of said ring device in a time-dependent manner to modify the rates of change of the amplitude and phase variables;
    mapping the amplitude and phase variables to an external observable variable to generate a physiologically-representative and observable output electrical stimulation signal; and
    stimulating said nonlinear biological system with said physiologically-representative and observable output electrical stimulation signal via an electromechanical interface.

13. The method of claim 12 wherein the kernels are Volterra or Wiener kernels that encode the dynamic response of the nonlinear biological system through a respective Volterra or Wiener functional series.

14. The method of claim 12 wherein each dynamic mode acts as an integrator, a differentiator or a combination thereof.

15. The method of claim 12 wherein said dynamic modes are neuronal modes selected from the group consisting of zero-order neuronal modes, first-order neuronal modes, second-order neuronal modes, third-order neuronal modes, and combinations thereof.

16. The method of claim 15 wherein each of the plurality of neuronal modes transforms a respective component of the input signal to yield a corresponding modal output.

17. The method of claim 12 further comprising scaling and combining modal outputs using a plurality of mixing functions prior to said applying.

18. The method of claim 12 wherein the biological system comprises a neuron.

19. The method of claim 12 wherein the biological system is a brain region.

20. The method of claim 19 wherein said brain region is stimulated to prevent, control or treat seizures.

\* \* \* \* \*